United States Patent [19]

Shepherd

[11] 4,211,783

[45] Jul. 8, 1980

[54] HYPOLIPIDEMIC AND ANTIATHEROSCLEROTIC NOVEL 4-(ARALKYL- AND HETEROARYLALKYLAMINO)PHENYL COMPOUNDS

[75] Inventor: Robert G. Shepherd, South Nyack, N.Y.

[73] Assignee: American Cyanamid Company, Stamford, Conn.

[21] Appl. No.: 890,569

[22] Filed: Mar. 20, 1978

[51] Int. Cl.$^2$ .................... C07C 95/08; A61K 31/11
[52] U.S. Cl. .......................... 424/263; 260/570.8 R; 260/326.16; 260/570.9; 260/347.8; 424/270; 424/272; 424/273 R; 424/274; 424/275; 424/285; 424/330; 542/422; 542/423; 546/329; 548/342; 548/236; 548/201; 549/77; 548/204

[58] Field of Search .................. 260/570.8 R, 570.9, 260/347.8, 326.16; 424/263, 270, 272, 273, 274, 275, 285, 330; 546/329; 542/423; 549/77

[56] References Cited

FOREIGN PATENT DOCUMENTS 1377226  9/1964  France ............................. 260/570.8 R

OTHER PUBLICATIONS

Berres et al. "p-Aminoarylaldehydes" in Chem. Abs. 7691f, vol. 62, 1965.

*Primary Examiner*—Arthur P. Demers
*Attorney, Agent, or Firm*—Robert P. Raymond

[57] ABSTRACT

This disclosure describes novel 4-(aralkyl- and heteroarylalkylamino)phenyl compounds useful as hypolipidemic and antiatherosclerotic agents.

8 Claims, No Drawings

HYPOLIPIDEMIC AND ANTIATHEROSCLEROTIC NOVEL 4-(ARALKYL- AND HETEROARYLALKYLAMINO)PHENYL COMPOUNDS

BRIEF SUMMARY OF THE INVENTION

This invention relates to new organic compounds and, more particularly, is concerned with 4-(aralkyl- and heteroarylalkylamino)phenyl compounds which may be represented by the following structural formula:

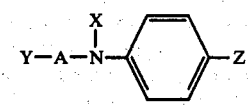

wherein A is a saturated or unsaturated alkylene group of 1-18 carbon atoms which may be branched or unbranched; Y is selected from the group consisting of substituted or unsubstituted aryl and heteroaryl groups, such that the total number of carbon atoms in Y and A shall not exceed 24; X is selected from the group consisting of hydrogen or a group convertible in vivo thereinto such as methyl, carboxymethyl, acetyl, succinyl, 1-(sodium sulfo)loweralkyl, 1-(sodium sulfo)-polyhydroxyloweralkyl, and 3-aryl-1,3-bis-(sodium sulfo)loweralkyl; and Z is (a)

wherein J is selected from the group consisting of hydrogen, loweralkyl, (mono- or polyhydroxy)loweralkoxy, (mono- or polycarboxy)loweralkoxy, (mono- or polycarboxy)hydroxyloweralkoxy, allyloxy, 2,3-epoxypropoxy, substituted or unsubstituted (phenoxy and 3-pyridyloxy), pyridylmethoxy, tetrahydropyranyloxy, (mono- or polyhydroxy)loweralkylamino, (mono- or polycarboxy)loweralkylamino, (mono- or polycarboalkoxy)loweralkylamino, allylamino, propargylamino, 2-sulfoethylamino, (substituted or unsubstituted aroyl)amino, loweralkanoylamino, loweralkanesulfonylamino, (substituted or unsubstituted arene)-sulfonylamino, loweralkanoylhydrazino, hydroxylamino, polymethyleneimino, (4-carboxy- or 4-carboethoxy)thiazolidino, and loweralkyl bearing one or more carboxy, carboloweralkoxy, carbamoyl, acyl, sulfinyl or sulfonyl groups, or (b)

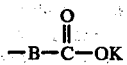

wherein B is a saturated or unsaturated loweralkylene group and K is selected from the group consisting of hydrogen, loweralkyl, loweralkoxyethyl, diloweralkylaminoethyl, (mono- or polyhydroxy)loweralkyl, (mono- or polycarboxy)loweralkyl, (mono- or polycarboxy)hydroxyloweralkyl, allyl, 2,3-epoxypropyl, substituted or unsubstituted (phenyl, benzyl or 3-pyridyl), pyridylmethyl and tetrahydropyranyl;

with the proviso that when A contains a carbon-carbon triple bond J may also be selected from the group consisting of hydroxy, loweralkoxy, loweralkoxyethoxy, diloweralkylaminoethoxy, and benzyloxy;

and the pharmaceutically acceptable, non-toxic acid-addition and cationic salts thereof. Lower whenever applied to alkane, alkanoyl, alkoxy, alkenyl, alkyl, alkylene or alkynyl refers to a hydrocarbon chain of 1-4 carbon atoms which may be branched or unbranched.

Suitable groups contemplated by the present invention for the aryl or heteroaryl moiety Y are phenyl, 4-methylphenyl, 3-methylphenyl, 4-decylphenyl, 3,4-dimethylphenyl, 4-methoxyphenyl, 4hexylphenyl, 4-tridecyloxyphenyl, 4-chlorophenyl, 4-fluorophenyl, 2-chloro-6-fluorophenyl, pentafluorophenyl, 1-naphthyl, 4-biphenylyl, 2-furyl, 2-thienyl, 2-butyl-4-thiazolyl, 2-imidazolyl, 2-undecyl-4-imidazolyl, 5-ethyl-2-furyl, 4-propyl-2-oxazolyl, 5-methyl-2-thienyl, and the like.

Suitable alkylene, alkenylene, and alkynylene groups contemplated for A are methylene, ethylene, hexamethylene, undecamethylene, hexadecamethylene, 3-methylheptamethylene, 2,7-dimethyloctamethylene, 9-decenylene, 4-hexenylene, 1-methyl-2-propenylene, 13-pentadecenylene, 18-methyl-18-octadecenylene, 6,8-nonadienylene, 10-undecenylene, 8-nonynylene, 16-heptadecynylene, 3hexynylene, 1-ethyl-2-tridecynylene, and the like.

Suitable esters contemplated by the present invention are those in which the group J is methoxy; isopropoxy; 2-ethoxyethoxy; 2-dimethylaminoethoxy; 1-methyl-4-piperidyloxy; 4-pyridylmethoxy; 2,3-dihydroxypropoxy; 2-hydroxypropoxy; 3-hydroxypropoxy; 4-chlorobenzyloxy; 3-methylbenzyloxy; 4-sulfophenoxy; 4-fluorophenoxy; 2,6-dichlorophenoxy; 3-carboxyphenoxy; 2,6-dimethyl-3-pyridyloxy; 6-methoxy-3-pyridyloxy; 2-hydroxy-3-pyridyloxy; 5-carboxy-3-pyridyloxy; 4-cyano-3-pyridyloxy; carboxymethoxy; 1-methoxycarbonylpropoxy; 2-methoxycarbonyl-2-propyl and the like.

Suitable amides contemplated are those in which the group J is 2,3-dihydroxypropylamino; carboxymethylamino, acetylamino, benzoylamino, 4-chlorobenzoylamino; methanesulfonylamino; phenylsulfonylamino, 1-piperidyl, and the like.

Suitable keto-acids and keto-esters contemplated by the present invention are those in which the group J is selected from the group consisting of carboxymethyl; carboxyethyl; 2-carboethoxy-2-propyl; dicarboethoxymethyl; carboethoxyvinyl and the like. Suitable alkanoic, alkenoic and alkynoic acids and esters are those in which the radical Z is selected from the group consisting of 4-carboxybutyl; 2-carboethoxyethyl; 2-carboxyvinyl, 2-carboethoxyethynyl, and the like.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel 4-(aralkyl and heteroarylalkylamino)phenyl compounds of the present invention. These compounds may be utilized either as such or in the form of a pharmaceutically acceptable salt with an organic or inorganic acid or base. The invention also contemplates a method for lowering serum lipids and for ameliorating atherosclerosis in mammals by the administration of said compounds.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 200 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine, and nicotinic acid [Levy and Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Related compounds are the subject of our copending U.S. patent application, Ser. No. 557,550.

DETAILED DESCRIPTION OF THE INVENTION

The compounds of this invention are new and novel 4-(aralkyl- and heteroarylalkylamino)phenyl compounds and have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These compounds provide the oral administration required of hypolipidemic agents, which patients usually take for many years. The novel compounds of this invention are adequately and reliably absorbed from the gastrointestinal tract with little, if any, gastrointestinal irritation.

We have now found that certain members of this class of compound can safely and effectively lower both serum-sterols and triglycerides in warm-blooded animals. Such actions on serum lipid components are considered to be very useful in the treatment of atherosclerosis, especially in contrast to available drugs whose action is much more limited. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warmblooded mammals for the treatment of hyperlipidemic and atherosclerotic states found in patients with or prone to heart attacks, to peripheral or cerebral vascular disease, and to stroke.

The 4-(aralkyl- and heteroarylalkylamino)phenyl compounds of the present invention are, in general, white crystalline solids having characteristic melting points and absorption spectra. They are soluble in organic solvents such as lower alkanols, chloroform, toluene, dimethylformamide, and the like but are generally not very soluble in water.

The novel compounds of the present invention which are organic bases may be converted to their non-toxic acid-addition salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, tartaric, ascorbic, and the like. Many of the novel compounds of the present invention which contain one or more acidic substituents may be converted to their organic or inorganic cationic salts for therapeutic use. The sodium or potassium salts which are formed in solution in the course of the above described hydrolyses reactions may be isolated as solids by cooling. When it is desirable to purify a compound in the form of the acid, the salt is conveniently formed by treating its solution with exactly one equivalent of base and evaporation or hyophylization. Alkaline earth salts are prepared similarly, often using their acetate salts as a conveniently soluble form. Organic base salts such as those of N-methylglucamine are prepared by dissolving equimolar amounts of the acid and the base in hot ethanol or aqueous alcohols and cooling the crystallization.

Many of the novel 4-(aralkyl- and heteroarylalkylamino)phenyl compounds of the present invention may be prepared by reaction of a 4-aminophenyl compound with a suitable alkylating agent such as an alkyl halide, sulfate, tosylate, or trifluoromethanesulfonate with or without a solvent at 30° C. to 150° C. Appropriate 4-aminophenyl compounds are, for example, ethyl 4-aminobenzoate; ethyl 3-(4-aminophenyl)propionate, 2,3-dihydroxypropyl 4-aminobenzoate; phenyl 4-aminobenzoate; 1-(4-aminobenzoyl)pyrrolidine; and ethyl 4-(4-aminophenyl)butyrate. Suitable solvents are lower alkanols, N,N-dimethylformamide, N,N-dimethylacetamide, 1,2-dimethoxyethane, acetonitrile, toluene, benzene, hexamethylphosphoramide and the like. The reaction may be carried out with two equivalents of the 4-aminophenyl compound or with one equivalent of the compound plus one equivalent of a base such as an alkali carbonate or bicarbonate or an unreactive base such as diisopropylethylamine or alternatively with a catalytic amount of copper powder when an alkyl halide is used as the alkylating agent. Similarly, alkylation of the sodium salt (formed with sodium hydride) of either the amino group of a 4-aminophenyl compound or the anilide moiety of a 4-(acetylamino)phenyl compound yields the novel 4-(aralkyl- and heteroarylalkylamino)phenyl compounds or an N-acetyl derivative thereof. Removal of the N-acetyl group by conventional hydrolytic methods affords the desired amino compounds.

Alternative methods of preparation of these compounds are by reductive alkylation of a 4-aminophenyl compound, which may be generated in situ by reduction of a 4-aminophenyl precursor such as a 4-nitrophenyl compound and the like or by a metal hydride reduction of a 4-(acylamino)phenyl compound. For example, 10-phenyldecanal or another carbonylalkane and ethyl 4-aminophenylacetate are reduced under 1-10 atmospheres of hydrogen using an activated metal catalyst or with a metal hydride such as sodium borohydride forming 4-(10-phenyldecylamino)phenylacetic acid and the like. Diborane reduction of 4-(aralkanoylamino)phenyl compounds such as ethyl 4-(11-phenylundecanoylamino)phenylacetate at room temperature or above for 1-6 hours yields the corresponding 4-(aralkylamino)phenyl compounds such as ethyl 4-(11-phenylundecylamino)phenylacetate. The 4-(aralkanoylamino)phenyl compounds used in these reductions are prepared by acylation of the appropriate 4-aminophenyl compounds with suitable acylating agents, such as aralkanoyl halides. To prepare the 4-(aralkyl- and heteroarylamino)phenyl alkenoic and alkynoic acids it is advantageous to form the corresponding alkylchloromide from the 4-(alkanoylamino)phenyl compounds using phosphorus oxychloride and base, and then reduce the alkylchloroimide moiety to an alkylamino group with sodium borohydride.

The 4-(aralkyl- and heteroarylalkylamino)benzoic and phenyl alkanoic acids of this invention are often prepared from the corresponding p-aminobenzoic and phenylalkanoic acids by the sequence invovling esterification of the amino acid with ethanol in the presence of boron trifluoride etherate, followed by alkylation of the amino function as described above. The free acids are then liberated by hydrolysis of the ester with aqueous alcoholic sodium hydroxide at 80° for 2-10 hours followed by acidification. The acids obtained by this procedure may be converted to the corresponding cationic salt. For example, the sodium salt may be prepared by reaction of the benzoic acid with the sodium hydroxide in a mixture of ethanol and water. Alternatively, the free acids may be prepared by hydrolysis of the corresponding nitriles or various amides, imidates or oxazolines. The carboxylic acid moiety may also be generated by oxidation of the corresponding aldehydes, acetophenones, benzyl alcohols, or toluenes, most often with the use of an amine-protecting group such as trifluoroacetyl or t-butyloxycarbonyl.

The carboxaldehydes of this invention may be prepared by several methods among which is alkylation of the corresponding acetals as described above followed by hydrolysis of the resulting 4-(aralkylamino)phenyl compound to the desired aldehyde. Aldehydes may also be prepared by reduction of the appropriate nitriles. For example, treatment of 4-(16-phenylhexadecylamino)hydrocinnamonitrile with stannic chloride and anhydrous hydrogen chloride gas, followed by hydrolysis in hot water provides 4-(16-phenylhexadecylamino)hydrocinnamaldehyde. These reductions are also conveniently carried out with hydrides such as diisobutylaluminum hydride.

The novel esters and amides of the present invention may readily be prepared by treating a derivative of the corresponding carboxylic acid, such as the acid halide, mixed acid anhydride or activated ester or amide with the appropriate alcohol or amine, respectively. These reactions may be carried out in an inert solvent at a temperature of 50°-125° C. for 30 minutes to 18 hours or more. In the case of the acid halide and other acid-forming acylating agents, the reaction is carried out in the presence of an acid scavenger such as diisopropylethylamine; 4-dimethylaminopyridine; pyridine; triethylamine; finely powdered sodium carbonate and the like. A protecting group on the amino nitrogen is used for best results. The simplest protecting group is provided by protonation of the amine to yield an anilinium salt prior to or during formation of the acylating form of the carboxyl group. Acylation of the amino group by carefully selected acyl groups such as carbobenzyloxy, carbo-t-butoxy, and trifluoroacetyl provides protection of this group from self-acylating during amide formation. These protecting groups are then removed by catalytic hydrogenation, mild acid treatment and mild alkali treatment, respectively. Other N-acyl protecting groups such as acetyl and succinoyl may be used and these are removed by conventional methods. Activated esters and amides, useful to synthesize the esters and amides of the present invention, are those containing carboxymethyl, 4-nitrophenyl, N-oxysuccinimide and 1-imidazolyl groups and the like. In certain cases, treatment of the acids with an excess of an appropriate hydroxy-containing substrate in the presence of a Lewis or mineral acid such as boron trifluoride, sulfuric acid or hydrochloric acid affords the corresponding esters. Ordinary esters such as the methyl and ethyl esters are sufficiently reactive to form the amides of the 4-(aralkyl- and heteroarylalkylamino)benzoic and phenylalkanoic acids and highly reactive amine substrates such as hydroxylamine, hydrazines and certain alkyl primary amines. In order to form amides from certain kinds of substrates, it is necessary first to form the alkali metal or strong organic base salts of these substrates prior to reacting them with the various aforementioned acylating forms of the 4-(aralkyl- and heteroarylalkylamino)-benzoic and phenylalkanoic acids. For example, the aminoalkanecarboxylic and aminoalkanesulfonic acids are zwitterionic and must be converted to their salts, suitably in situ. They may also be used in the form of their esters and then hydrolyzed after amide formation. Certain substrates which are neutral, like the carboxamides, or slightly acidic, like the alkane or arene sulfonamides, are converted to acylatable sodium salts by reaction with sodium hydride or other basic reagents.

The α-substituted 4-(aralkyl- and heteroarylalkylamino)acetophenones of the invention are prepared by reaction of a derivative of the appropriate benzoic acid, such as 4-(11-phenylundecylamino)benzoyl chloride hydrochloride, with two or more equivalents of the reactive salt of an acidic methylene compound, for example the sodium salt of diethyl malonate. Other benzoic acid derivatives are also suitable for this reaction, such as an N-trifluoroacetyl or N-tert-butyloxycarbonyl cid chloride, or a methyl ester of the acid. In some cases the final step in the preparation of the α-substituted 4-(aralkyl- and heteroarylalkylamino)acetophenone is the removal of the nitrogen-protecting group. In other cases, hydrolysis of one or more of the ester groups in the acylation product affords an unstable polycarboxylic acid which undergoes decarboxylation to allow the preparation of another acetophenone derivative. For example, the reaction of tert-butyl ethyl [4-(11-phenylundecylamino)benzoyl]malonate with trifluoroacetic acid affords ethyl [4-(11-phenylundecylamino)benzoyl]acetate. In other cases, hydrolysis of one or more of the ester groups allows the preparation of the corresponding acid derivative. For example, the hydrolysis of ethyl [4-(6-phenylhexylamino)benzoyl]acetate yields [4(6-phenylhexylamino)benzoyl]acetic acid.

An alternative procedure for preparing certain α-substituted-4-(aralkyl- and heteroarylalkylamino)acetophenones is alkylation of the corresponding 4-aminoacetophenone by the methods above. For example, alkylation of methyl 3-(4-aminobenzoyl)propionate with 11-phenylundec-10-bromide yields methyl 3-[11-phenylundec-10-enylamino)benzoyl]propionate. The related carboxylic acids are then obtained by hydrolysis. Certain of these acids are particularly useful for the preparation of 4-(aryl- and heteroarylalkylamino)-phenyl]alkanoic acids by reduction. For example, the Clemmensen or Wolff-Kishner reduction of 3-[4-(6-phenylhexylamino)benzoyl]propionic acid yields 4-[4-(6-phenylhexylamino)phenyl]butyric acid.

The 4-(aryl- and heteroarylalkylamino)phenylalkenoic acids may be prepared by condensation of the appropriate aldehydes or by dehydration of the corresponding substituted-phenylhydroxyalkanoic acids. For example, ethyl 5-[4-(benzylamino)phenyl]-2,4-pentadienoate is obtained by the Wittig reaction of 4-(benzylamino)benzaldehyde with the Wittig reagent, triethyl 4-phosphonocrotonate. Alternatively, these alkenoic acids are obtained by heating 4-8 N-(10-phenyldecyl-N-methylamino]benzaldehyde and the like with the sodium salt of the carbanion of ethyl acetate or with a mixture of ethyl acetate, acetic anhydride and potassium acetate. The second method is illustrated by dehydration of ethyl 3-[(4-benzylamino)phenyl]-3-hydroxypropionate to yield ethyl 4-benzylaminocinnamate.

The acetylenic analogs are prepared by dehydrobromination of the side-chain vic-dibrominated alkanoic acid. For example, dehydrobromination of ethyl 3-[(4-benzylamino)phenyl]-2,3-dibromopropionate, its isomers or N-acyl analogs or of ethyl 3-[(4-benzylamino)phenyl]-3-bromoacrylate yields ethyl 4-(benzylamino)-phenylpropiolate. The acetylenic acids are also formed from (4-benzylamino)phenylacetylene metal salts by carboxylation with carbon dioxide. The 4-(aryl- and heteroarylalkylamine)phenylacetylenes are also used by N-acylating with t-butyl azidoformate followed by conversion to the lithium acetylide salt and the subsequent reaction of the lithium salt with boron trifluoride etherate in tetrahydrofuran at −20° C. to form tris-[(4-substituted-alkylamino)phenylethynyl]boranes. The tetrahydrofuran solution of the borane is in turn reacted with ethyl diazoacetate, followed by water to yield ethyl 4-[(4-monoalkylamino)phenyl]butynoate.

The 4-(aralkyl- and heteroarylalkylamino)phenylalkanoic acids, amides, or esters are also prepared by catalytic reduction at 1 to 10 atmospheres of hydrogen of the corresponding alkenoic or alkynoic acid derivatives. The 4-(aryl and heteroarylalkylamino)phenylalkenoic acids and derivatives are prepared by Friedel-Crafts acylation of the N-acyl-N-alkylanilines with the appropriate dicarboxylic acid anhydride or half acid chloride. The 4-(aryl and heteroarylalkylamino)benzoylalkanoic acids or esters, obtained by this and by other syntheses, may be converted to the corresponding 4-(substituted-amino)phenylalkanoic acids by reduction with (a) hydrazide and alkali in diethylene glycol at 140° for 3 hours, (b) zinc amalgam and ethanolic hydrochloric acid at 60° for 5 hours, (c) red phosphorus and hydriodic acid, or (d) ketalization with 1,2-ethanedithiol followed by Raney nickel desulfurization. The amides of these 4-(substituted-amino)phenylalkanoic acids are prepared by heating the corresponding 4-(substituted-amino)phenylalkyl ketones with aqueous alcoholic ammonium polysulfide followed by hydrolysis to yield the acids with the same number of carbon atoms as the ketone. These acids are also prepared by reacting 4-(N-t-butyloxycarbonyl-N-aralkyl- and heteroarylalkylamino)phenylmagnesium halides with 2-(3-halopropyl)-2-oxazolines, followed by mild acid removal of 2-oxazolinyl and t-butoxycarbonyl protecting groups. Similarly, the above Grignard reagent can be reacted with 3-bromotriethylorthopropionate in the presence of dilithiumtetrachlorocuprate to yield the desired acids after removal of the protecting groups from the amino and carboxyl groups.

The novel 4-(aralkyl- and heteroarylalkylamino)phenyl compounds of the present invention are not only potent hypolipidemic agents but also prevent or diminish the formation of enlargement of arterial plagues in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound, for a subject of about 70 kg. of body weight, are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholesteremic and antiatherosclerotic effect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate, a disintegrating agent ush as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propyl parabens as preservatives, a dye, and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjunction with the following specific Examples.

EXAMPLE 1

Preparation of 4-(4-methoxyphenyl)-1-butyne

A solution of 39.2 g. of zinc dust, 157 g. of triphenylphosphene and 200 g. of carbon tetrabromide in 500 ml. methylene chloride is stirred at room temperature for 25 hours. To the resultant solution is added 50 g. of 4-methoxyhydrocinnamaldehyde and stirring is continued for an additional 2 hours. The solution is diluted with 2 l. of pentane and the precipitate is filtered. The precipitate is stirred with 100 ml. methylene chloride, diluted with 400 ml. pentane, and again filtered. The organic solutions are combined and evaporated to yield 1,1-dibromo-4-(4-methoxyphenyl)-1-butene as a light yellow oil.

A solution of 40 g. of the yellow oil in 700 ml. dry tetrahydrofuran is cooled to $-78°$ in a dry ice-acetone bath and treated with 220 ml. of 1.16 M n-butyllithium in pentane. The solution is stirred at $-78°$ for 1 hour, warmed, and stirred an additional hour at room temperature. The reaction is poured slowly into 1 l. water and the mixture is extracted twice with 500 ml. methylene chloride. The solution is dried with magnesium sulfate and evaporated and the residue is distilled to yield the product as a colorless crystalline mass.

EXAMPLE 2

Preparation of 16-bromohexadecanoic acid

To a stirred solution of 102 gm. 16-hydroxyhexadecanoic acid in 720 ml. 32% hydrobromic acid in acetic acid is slowly added 180 ml. sulfuric acid. After stirring at room temperature overnight the solution is refluxed for 3 hours. An additional 180 ml. solvent is added and reflux is resumed for an additional 4 hours. The warm solution is slowly poured into 2 l. of stirred ice-water, the precipitate is collected and thoroughly washed with water. Crystallization from acetonitrile yields 16-bromohexadecanoic acid as white crystals.

EXAMPLE 3

Preparation of 11-bromoundecanol

A 250 ml. of solution of 1 M borane in tetrahydrofuran is cooled in an ice-water bath, and to this is slowly added 50 g. 11-bromoundecanoic acid in 150 ml. dry tetrahydrofuran. After stirring at room temperature for 19 hours the reaction is quenched by the addition of 300 ml. 10% hydrochloric acid. The aqueous solution is extracted three times with 150 ml. portions of ether, the organic layers are combined, washed with saturated brine, dried with anhydrous magnesium sulfate and evaporated. Distillation of the residue yields 11-bromoundecanol as a colorless liquid.

EXAMPLE 4

Preparation of 11-bromo-1-(p-toluenesulfonyloxy)undecane

A solution of 30 g. 11-bromoundecyl alcohol and 25.0 g. 4-toluenesulfonyl chloride in 250 ml. dry ether is cooled with stirring in an ice-water bath. To this is added dropwise 13.2 g. triethylamine in 50 ml. ether. After addition, the solution is stirred in the cold for 1 hour and filtered. The ether is washed with 100 ml. 10% hydrochloric acid solution, 100 ml. brine, dried and evaporated to yield the title compound as an oily solid.

EXAMPLE 5

Preparation of 13-(4-chlorophenyl)-12-tridecynyl bromide

To a stirred solution of 200 ml. 1M ethyl magnesium bromide in ether under a stream of argon is added dropwise a solution of 25.9 g. 4-chlorophenylacetylene in 100 ml. ether. The solution is stirred at reflux for 3 hours (until gas evolution ceases) and most of the ether is distilled. Toluene (500 ml.) is added and distillation of ether is continued until the reaction temperature reaches 80°. Heating is discontinued and a solution of 77 g. 11-bromo-1-(p-toluenesulfonyloxy)undecane in 50 ml. toluene is slowly added. The solution is stirred at 80° for 16 hours, cooled, and quenched by the addition of 200 ml. 50% acetic acid. The layers are separated and the organic layer is washed with 200 ml. saturated bicarbonate solution, 200 ml. water, dried and evaporated. Distillation of the residue yields the title compound as a colorless liquid.

EXAMPLE 6

Preparation of ethyl 4-[13-(4-chlorophenyl)-12-tridecynylamino]benzoate

A solution of 20 g. 13-(4-chlorophehyl)-12-tridecynyl bromide and 17.8 g. ethyl 4-aminobenzoate in 75 ml. hexamethylphosphoramide is stirred at 115° for 17 hours. The cooled solution is diluted with 150 ml. water, the precipitate is filtered, washed in portions with 250 ml. 50% ethanol and dried to a tan solid. The product is dissolved in 200 ml. warm methylene chloride, passed through a pad of magnesol, and the solution is evaporated. Crystallization from 300 ml. acetonitrile yields colorless crystals of the title compound.

EXAMPLE 7

Preparation of 4-[13-(4-chlorophenyl)-12-tridecynylamino]benzoic acid

A 4 g. sample of ethyl 4-[13-(4-chlorophenyl)-12-tridecylamino]benzoate is hydrolyzed with 1.6 g. 85% potassium hydroxide in 60 ml. 95% ethanol by refluxing the solution for 5 hours. The solution is cooled, diluted with 100 ml. water and acidified to pH 4.5 with 37% hydrochloric acid. The precipitate is collected, dried in vacuo and crystallized from acetone to yield the title compound as a white powder.

EXAMPLE 8

Preparation of 4-(4-fluorophenyl)-3-butyn-1-ol

A solution of ethylmagnesium bromide is prepared by reacting 68 g. ethyl bromide with 16.2 g. magnesium ribbon in 200 ml. dry ether. After preparation of the Grignard reagent is completed, 200 ml. dry toluene is added and the ether is distilled, the solution is cooled and 60 g. 4-fluorophenyl acetylene in 30 ml. toluene is added dropwise at a rate such that the reaction temperatures does not exceed 10°. After addition is completed, the solution is warmed at 90° for 5 hours. The reaction is again cooled in an ice bath and 31 g. ethylene oxide is passed into the stirred gray colution and stirring is continued at ambient temperature for 18 hours. After 4 hours of reflux, most of the toluene is distilled. The cooled solution is treated with 300 ml. water and 300 ml. 20% sulfuric acid, extracted twice with 500 ml. portions methylene chloride, and the combined organic layers are washed with 200 ml. saturated bicarbonate solution. After drying and evaporation, the residue is distilled to yield the title compound as a colorless liquid.

EXAMPLE 9

Preparation of 4-(4-fluorophenyl)-1-methanesulfonyloxy-3-butyne

To a mixture of 250 ml. of dichloromethane, 25 g. 4-(4-fluorophenyl)-3-butyn-1-ol and 16.7 g. of triethylamine cooled in an ice-salt bath to −10° C. is added dropwise, over 15 minutes, 18.9 g. of methanesulfonyl chloride. The mixture is cooled at −10° C. to −15° C. for 30 minutes and then washed with 300 ml. each of cold water, 10% hydrochloric acid, sodium carbonate solution and with saturated sodium chloride solution. The organic layer is dried with magnesium sulfate and concentrated in vacuo to give a pale yellow oil.

EXAMPLE 10

Preparation of ethyl 4-[4-(4-fluorophehyl)-3-butynylamino]benzoate

A solution of 10 g. 4-(4-fluorophenyl)-1-methanesulfonyloxy-3-butyne and 13.6 g. ethyl 4-aminobenzoate in 50 ml. hexamethylphosphoramide is heated at 120° for 18 hours. The partially-cooled (about 50°) solution is diluted with 100 ml. water and the resultant precipitate is collected. After washing in portions with 200 ml. 50% ethanol, the tan product is dried in vacuo and crystallized three times from ethanol to yield the title compound as colorless crystals.

EXAMPLE 11

Prepartion of ethyl 4-[3-(4-chlorophenyl)prop-2-enylamino]phenylacetate

To a cold (−20°) stirred solution of 10.8 g. 4-chlorocinnamyl alcohol prepared by lithium aluminum hydride reduction of methyl 4-chlorocinnamate and 13.4 ml. triethylamine in 300 ml. ether is added dropwise 5.6 ml. methanesulfonyl chloride in 5 ml. of ether. After addition is completed, the solution is warmed to room temperature, stirred for 30 minutes and filtered directly into a solution of 23.1 g. ethyl 4-aminobenzoate in 100 ml. ether. After 17 hours at room temperature, the precipitate is filtered and washed with several portions of methane chloride. The organic solution is washed twice with 100 ml. water, 100 ml. brine, dried and evaporated. The tan residue is crystallized from ethanol and from acetonitrile to yield the title compound as white crystals.

EXAMPLE 12

Preparationof 5-octyl-2-thiophenecarboxaldehyde

To a stirred solution of 80.1 g. of 2-octylthiophene in 70 ml. dimethylformamide is added dropwise 42.4 ml. of phosphorus oxychloride. After addition, the solution is made warmed at 100° for 1 hour, then poured into 600 ml. ice. After neutralization with sodium acetate, the resulting oil is extracted with ether. The ether is washed with water and aqueous potassium carbonate, dried, and distilled in vacuo to give the title compound as an oil.

EXAMPLE 13

Preparation of ethyl 4-[2-(5-octylthienyl)methylamino]hydrocinnamate

A solution of 8.6 g. ethyl 4-aminohydrocinnamate, 9.77 g. 5-octyl-2-thiophenecarboxaldehyde and a few crystals of 2,4-dinitrobenzenesulfonic acid in 250 ml. toluene is refluxed under a Dean-Stark trap for 17 hours, whereupon the theoretical amount (0.8 ml.) water has been collected. The toluene is evaporated to yield ethyl 3-[4-(5-octyl-2-thienylideneamino)phenyl]-propionate as a crystalline mass.

To a mixture of 17.8 g. of the above compound in 250 ml. ethanol is added 1.68 g. sodium borohydride and the mixture is stirred at room temperature for 18 hours. Excess reagent is decomposed by addition of 10 ml. acetic acid. The solution is concentrated in vacuo and the residue is partitioned between toluene and aqueous potassium carbonate. After drying, the toluene is evaporated to yield a solid. Crystallization from acetonitrile and from ethanol affords the title compound as white crystals.

EXAMPLE 14

Preparation of ethyl 4-aminophenylpropiolate

A sample of 50 g. of ethyl p-aminocinnamate is dissolved in 500 ml. of ethyl ether and a solution of 28 g. of acetic anhydride in 30 ml. of ether is added dropwise. When the addition is complete, the reaction is allowed to stir for another hour. The mixture is then diluted with hexane and filtered, providing ethyl p-acetamidocinnamate.

A solution of 40 g. of ethyl p-acetamidocinnamate in 200 ml. of carbon tetrachloride is cooled in ice. Bromine (28 g.) is added dropwise, the reaction is allowed to stir for one additional hour, and then the solvent is evaporated. The crystalline residue is the dibromo ester.

A solution of 11.4 g. of potassium hydroxide in 300 ml. of 95% ethanol is cooled to 40° C. and 20 g. of the crude dibromo ester above is added. After 30 minutes, the reaction is heated to reflux for five hours. The solution is then cooled and filtered. The filtrate is treated with acetic acid until the solvent is neutral to litmus then concentrated, chilled and filtered, to yield ethyl 4-aminophenylpropiolate.

EXAMPLE 15

Preparation of ethyl 5-octylthiophene-2-acrylate

A solution of 75.4 g. 5-octyl-2-thiophenecarboxaldehyde and 117.6 g. ethyl (triphenylphosphoranylidene)acetate in 400 ml. tetrahydrofuran is refluxed for 20 hours. The solution is concentrated, the semi-solid residue is slurried with ether and filtered. Concentration followed by distillation of the resultant oil yields ethyl 5-octylthiophene-2-acrylate as an oil.

EXAMPLE 16

Preparation of (10-carboxydecyl)triphenylphosphonium bromide

A solution of 81.4 g. 11-bromoundecanoic acid and 85.0 g. triphenylphosphine in 600 ml. acetonitrile is refluxed for 64 hours, then concentrated in vacuo. The resultant oil is dissolved in 200 ml. ether, whereupon crystals of the title compound form.

EXAMPLE 17

Preparation of 12-(2-thienyl)-11-dodecenol

To a stirred slurry of 18.1 g. lithium aluminum hydride in 460 ml. ether is added dropwise a solution of 61.3 g. 12-(2-thienyl)-11-dodecenoic acid in 140 ml. ether at a rate such that gentle reflux is maintained. After four additional hours at reflux, the solution is cooled in ice and treated sequentially with 18.1 ml. water, 18.1 ml. 15% sodium hydroxide, solution and 54.3 ml. water. The precipitate is filtered and washed several times with ether. The combined ether fractions are washed with brine, dried, and evaporated. Distillation of the residual yields 12-(2-thienyl)-11-dodecenol as a semicrystalline mass.

EXAMPLE 18

Preparation of 6-(2-furyl)-5-hexenoic acid

To a cooled solution of dimsyl sodium (prepared by heating 4.35 g. of 50% oil dispersion of sodium hydride in 50 ml. dimethylsulfoxide at 60° for 2 hours under argon) is added dropwise 20.0 g. of (4-carboxybutyl)triphenylphosphonium bromide in 90 ml. dimethylsulfoxide. After the solution has stirred at room temperature for one hour, a solution of 4.34 g. furfural in 20 ml. dimethylsulfoxide is added dropwise to the cool (15°) solution over 20 minutes. After 2 hours the dimethylsulfoxide is evaporated, the residue is dissolved in 100 ml. water, filtered and extracted four times with 150 ml. portions of ethyl acetate. The aqueous solution is acidified to pH 1 with 1 N hydrochloric acid, saturated with sodium chloride and extracted twice with 150 ml. portions of ethyl ether. The ether is dried and evaporated to yield the title compound as a yellow oil.

EXAMPLE 19

Preparation of 6-(2-furyl)hexanoic acid

Nine grams 6-(2-furyl)-5-hexenoic acid is dissolved in 50 ml. acetic acid, 1.8 g. 10% palladium-on-charcoal is added, and the solution is hydrogenated at 40 p.s.i. for 16 hours. The catalyst is filtered, the solvent evaporated, and the residue is dissolved in 200 ml. ether. The solution is washed twice with 25 ml. portions of saturated sodium bicarbonate, dried, and evaporated to a light yellow oil.

In some cases when reduction is incomplete under the above conditions, fresh catalyst is added and hydrogenation is continued. For reduction of substrates containing a sulfur moiety, an equal weight of passadium-on-barium sulfate is used as catalyst.

EXAMPLE 20

Preparation of ethyl 4-[11-(1-imidazolyl)undecylamino]phenylacetate

To a stirred mixture of 4.84 g. of hexane-washed 50% sodium hydride dispersion in 70 ml. hexamethylphosphoramide is added a solution of 7.23 g. imidazole in 20 ml. hexamethylphosphoramide and the mixture is stirred at room temperature for 2 hours. A solution of 20.7 g. ethyl 4-(11-bromoundecylamino)phenylacetate in 20 ml. hexamethylphosphoramide is then added and the reaction mixture is stirred for 64 hours at ambient temperature, the solution is poured into 1.5 l. water and extracted twice with 1.5 l. portions of ethyl acetate. The organic layers are combined, washed twice with water, dried with magnesium sulfate and evaporated. The product is purified by crystallization from acetonitrile.

EXAMPLE 21

Preparation of 2-undecyl-4-hydroxymethylimidazole

A solution of 100 g. undecylcyanide in 100 ml. dry ethanol and 400 ml. ether is cooled in an ice bath and 60 g. hydrogen chloride is bubbled in. After 16 hours at 0°, the solvents are evaporated and 1 l. ether is added. The resultant white precipitate is collected and placed into a bomb reactor. The bomb is charged with 46.9 g. dihydroxyacetone and 500 ml. liquid ammonia. After heating at 60° for 5 hours, the ammonia is evaporated and 500 ml. saturated aqueous potassium carbonate is added. The precipitate is collected and crystallized from acetonitrile-methanol and from ethanol to yield the title compound as white crystals.

EXAMPLE 22

Preparation of 2-undecyl-4-chloromethylimidazole hydrochloride

Into a solution of 2.5 g. 2-undecyl-4-hydroxymethylimidazole in 25 ml. ethanol is bubbled hydrogen chloride gas to saturation. The ethanol is evaporated and the residue is re-dissolved in 25 ml. toluene, 2 ml. thionyl chloride is added and the solution is refluxed for 2 hours. Evaporation yields the title compound as an oil.

EXAMPLE 23

Preparation of ethyl 4-[6-(4-chlorophenyl)hexa-5-enylamino]phenylacetate

To a solution of 10.0 g. ethyl 4-[6-(4-chlorophenyl)-hexa-5-ynylamino]phenylacetate in 75 ml. acetone is added 1.0 ml. quinoline and 0.2 g. of palladium-on-calcium carbonate. The solution is hydrogenated at slightly above atmospheric pressure until 600 ml. hydrogen has been absorbed. The catalyst is filtered and washed with several small portions of acetone. The organic solution is diluted with 200 ml. water, the precipitate is collected, dried, and recrystallized from acetonitrile to yield the title compound as white crystals.

EXAMPLE 24

Preparation of 4-chlorocinnamyl alcohol

A solution of 30 g. methyl 4-chlorocinnamate in 300 ml. dry ether is cooled to −20° in a dry ice-acetone bath, then with stirring, 3.3 g. lithium aluminum hydride is added in portions at a rate such that the reaction temperature does not exceed −10°. After addition is complete, the reaction is allowed to warm slowly and stirring is continued for 18 hours at room temperature. The solution is treated in sequence with 3.3 ml. water, 3.3 ml. 15% aqueous sodium hydroxide and 9.9 ml. water. After stirring for one hour, the yellow precipitate is filtered and washed with several small portions of ether. Evaporation of solvent yields the product as a light yellow oil which on distillation affords 4-chlorocinnamyl alcohol as a white solid.

EXAMPLE 25

Preparation of 4-(4-methoxyphenyl)-1-butanol

A flask containing 250 ml. 1 M diborane in tetrahydrofuran is thoroughly cooled in an ice-water bath. To the stirred solution is slowly added 38.8 g. of 4-(4-methoxyphenyl)butyric cid in 100 ml. tetrahydrofuran. After addition is completed the reaction is stirred for 16 hours at room temperature, then poured slowly into 1 l. stirred ice-water. The aqueous solution is extracted three times with 300 ml. portions of ether. The combined organic extracts are washed with water and brine, dried, and evaporated to a nearly colorless oil of 4-(4-methylphenyl)-1-butanol.

EXAMPLE 26

Preparation of 13-(4-methoxyphenyl)tridecyl bromide

A solution of 3-(4-methylphenyl)propylmagnesium bromide is prepared by reacting 20 g. 3-(4-methylphenyl)propyl bromide with 2.5 g. of magnesium turnings in 50 ml. dry tetrahydrofuran. The solution of Grignard reagent is added dropwise to a stirred, cold (−10° C.) solution of 30 g. of 1,10-dibromodecane and 0.2 g. of lithium tetrachlorocuprate in 75 ml. dry tetrahydrofuran at a rate such that the reaction temperature does not exceed −5° C. After one addition hour of stirring at −10° C., the solvent is evaporated and the resultant liquid is fractionated in vacuo to yield 13-(4-methylphenyl)tridecyl bromide as a colorless liquid.

EXAMPLE 27

Preparation of ethyl 3-{4-[7-(3-bromophenyl)hepta-6-enylamino]phenyl}-propionate A mixture of 5.0 g. of ethyl 4-aminohydrocinnamate, 10.0 g. of 7-(3-bromophenyl)-1-methanesulfonyloxy-6-heptene (prepared by the method of Example 9), 4.2 g. of anhydrous powdered potassium carbonate and 40 ml. hexamethylphosphoramide is heated to 80° for 17 hours. The mixture is then cooled, diluted with water and extracted with ethyl ether. The ether extracts are washed with water, dried and evaporated. The residue is recrystallized from ethanol yielding the title compound as white crystals.

EXAMPLE 28

Preparation of ethyl 4-[13-(4-chlorophenyl)tridecylamino]-cinnamate

A mixture of ethyl p-aminocinnamate, 5.9 g. 13-(4-chlorophenyl)tridecyl bromide and one equivalent of anhydrous powdered potassium carbonate in 50 ml. hexamethylphosphoramide is heated for 20 hours at 60° C. The mixture is then cooled, diluted with water and extracted with ether. The combined ether extracts are dried, filtered and evaporated. Crystallization from acetonitrile provides the title compound as white crystals.

EXAMPLE 29

Preparation of 4-[10-(2-thienyl)deca-9-enylamino]benzophenone p-Aminoacetophenone is heated with 5 g. 10-(2-thienyl)-1-methanesulfonyloxy-9-decene (prepared by the method of Example 9) in 50 ml. hexamethylphosphoramide containing anhydrous potassium carbonate (1.9 g.) for 16 hours a 100° C. The solution is cooled to room temperature, filtered to remove solids, and the filtrate is diluted with cold water (50 ml.). The amber solid so obtained is collected and washed with water. Recrystallization from ethanol followed by dichloromethane provides the title compound.

EXAMPLE 30

Preparation of 4-[10-(4-methoxyphenyl)decylamino]benzonitrile

4-Aminobenzonitrile (11.8 g.) and 10-(4-methoxyphenyl)decylbromide (16.3 g.) are dissolved in hexamethylphosphoramide (100 ml.) and heated under nitrogen in an oil bath maintained at 120° C. for 22 hours. The reaction mixture is cooled to room temperature and water (100 ml.) is added gradually. The mixture is then chilled in an ice bath. The precipitate separated is filtered, washed thoroughly with water, and dried. It is then washed repeatedly with hexane and dried. Recrystallization from ether-hexane affords 4-[10-(4-methoxyphenyl)decylamino]benzonitrile as pale yellow crystals.

EXAMPLE 31

Preparation of 4-[10-(4-methoxyphenyl)decylamino]benzaldehyde

Di-isobutylaluminum hydride (54 ml., 25% solution in toluene) is added with stirring to a solution of 12.1 g. of 4-[10-(4-methoxyphenyl)decylamino]benzonitrile under a nitrogen atmosphere. After addition is completed, the solution stirred for one hour. A solution of methanol in toluene (50 ml., 1:1) is added over 30 minutes and the mixture is poured into 500 ml. vigorously stirred ice-cold 50% aqueous sulfuric acid. The mixture is filtered and the organic layer separted. The aqueous solution is extracted twice with toluene (100 ml.) and the combined organic layers are washed with aqueous sodium bicarbonate, dried over magnesium sulfate, decolorized with charcoal, filtered and evaporated in vacuo to give a light yellow crystalline solid. The product is recrystallized from dichloromethane/hexanes giving colorless needles.

EXAMPLE 32

Preparation of sodium 4-[13-(4-Chlorophenyl)tridec-12-ynylamino]benzoate

A mixture of 3.62 g. of 4-[13-(4-chlorophenyl)tridec-12-ynylamino]benzoic acid (Example 7) and 25 ml. of ethanol-water (9:1) containing 0.400 g. of sodium hydroxide is stirred for 4 hours. The mixture is filtered and the residue washed with 10 ml. of ethanol-water (9:1) and dried in vacuo for 24 hours to yield sodium 4-[13-(4-chlorophenyl)tridec-12-ynylamino]benzoate as a white solid.

EXAMPLE 33

Preparation of 4-[13-(4-chlorophenyl)tridec-12-ynylamino]benzoyl chloride

A cold solution of 25 g. 4-[13-(4-chlorophenyl)tridec-12-ynylamino]benzoic acid in 500 ml. dimethoxyethanemethylene chloride (4:1) is prepared and dry hydrochloric acid is bubbled through the solution until no more precipitate forms. The solution is treated with 25 ml. thionyl chloride and refluxed until all of the precipitate has dissolved. The solvents are evaporated to yield the acid chloride hydrochloride as an orange, semicrystalline mass.

EXAMPLE 34

Preparation of 4-[N-trifluoroacetyl-13-(4-chlorophenyl)tridec-12-ynylamino]benzoyl chloride A stirred ice-cold suspension of 9 g. 4-[13-(4-chlorophenyl)tridec-12-ynylamino]benzoic acid in 100 ml. of dimethoxyethane and 16 ml. of pyridine is treated with 18 ml. of trifluoroacetic anhydride at 0° C. The solution is stirred for 30 minutes at room temperature and then diluted with 300 ml. ether and 100 g. ice. After stirring vigorously for 15 minutes, the phases are separated, the ether solution is washed with brine, dried and evaporated to a white, amorphous solid.

To a solution of 9.2 g. of the above solid in 30 ml. methylene chloride and 0.5 ml. dimethylformamide is added 5.7 ml. thionyl chloride. After 20 hours at reflux, the solvents are evaporated to yield 4-[N-trifluoroacetyl-13-(4-chlorophenyl)tridec-12-ynylamino]benzoyl chloride as a light yellow, mobile oil.

EXAMPLE 35

Preparation of 4-[N-carbobenzyloxy-13-(4-chlorophenyl)tridec-12-ynylamino]benzoyl chloride To 15 g. 4-[13-(4-chlorophenyl)tridec-12-ynylamino]benzoic acid in 200 ml. warm chloroform is added a solution of 12 g. sodium carbonate in 150 ml. water. To the vigorously stirred solution is added 10 g. carbobenzyloxy chloride. After 2 hours stirring at 40° C., the layers are separated, washed three times with 1N hydrochloric acid, dried, and evaporated to an oil. The oil is dissolved in 300 ml. toluene, treated with 15 ml. thionyl chloride and the solution is refluxed for 5 hours. The solvents are evaporated and the residue is dissolved three times in toluene, evaporating each time ultimately to yield 4-[N-carbobenzyloxy-13-(chlorophenyl)tridec-12-ynylamino]benzoyl chloride as a viscous, orange oil.

EXAMPLE 36

Preparation of 1{4-[(N-tert-butyloxycarbonyl)-13-(4-chlorophenyl)tridec-12-ynylamino]benzoyl}imidazole To a solution of 10 g. 4-[13-(4-chlorophenyl)tridec-12-ynylamino]benzoic acid in 100 ml. dioxane is treated with 4.0 g. tert-butylazidoformate and 10 ml. pyridine. After stirring at room temperature for 18 hours, the protected amidoacid is precipitated from solution by the addition of 150 ml. water. The solid is collected, thoroughly dried, and dissolved in 200 ml. of a mixture consisting of methylene chloride/dimethoxyethane/pyridine (1:4:1). To this solution is added 5.4 g. 1,1'-carbonyldiimidazole. The solution is stirred overnight at room temperature and the solvents are evaporated to yield 1-{4-[(N-tert-butyloxycarbonyl)-13-(4-chlorophenyl)tridec-12-ynylamino]benzoyl}imidazole and an orange oil.

EXAMPLE 37

Preparation of 2,3-dihydroxypropyl 4-[13-(4-chlorophenyl)tridec-12-ynylamino]benzoate A solution of 7.34 g. of 4-[13-(4-chlorophenyl)tridec-12-ynylamino]benzoic acid, 4.80 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield 2,3-dihydroxypropyl 4-[13-(4-chlorophenyl)tridec-12-ynylamino]benzoate.

EXAMPLE 38

Preparation of methyl 4-[13-(4-chlorophenyl)tridec-12-ynylamino]benzoate

A solution of 20.7 g. of 4-[13-(4-chlorophenyltridec-12-ynylamino]benzoic acid in 25 ml. of hexamethylphosphoramide is added to a stirred mixture of 0.800 g. of sodium hydride (57% in mineral oil) and 25 ml. of hexamethylphosphoramide. The solution which forms after one hour is treated with 11.0 g. of methyl iodide and is then stirred at 25° C. for 18 hours. Dilution with water followed by filtration affords a white solid which is crystallized from ethanol to yield methyl 4-[13-(4-chlorophenyl)tridec-12-ynylamino]benzoate as a white solid.

EXAMPLE 39

Preparation of 3-hydroxypropyl 4-[13-(4-chlorophenyl)tridec-12-ynylamino]benzoate A mixture of 2.25 g. of methyl 4-[13-(4-chlorophenyl)tridec-12-ynylamino]benzoate, 280 mg. of 1,3-propanediol and 1.37 g. p-toluenesulfonic acid is heated at 180° C. for 18 hours and then is partitioned between ether and 3% aqueous sodium carbonate solution. The ether layer is separated, dried, and evaporated to yield 3-hydroxypropyl 1,3-propanediol 4-[13-(4-chlorophenyl)tridec-12-ynylamino]benzoate.

EXAMPLE 40

Preparation of 2-ethoxyethyl 4-[13-(4-chlorophenyl)tridec-12-ynylamino]benzoate

A solution of 11.8 g. of 4-[13-(4-chlorophenyl)tridec-12-ynylamino]benzoic acid, 1.00 g. of 2-ethoxyethanol and 5.35 ml. of boron trifluoride etherate in 200 ml. toluene is stirred under reflux for 48 hours. The solution is treated with an additional 5.35 ml. of boron trifluoride etherate and refluxing is continued for 120 hours. Dilution with water and methylene chloride followed by filtration affords 2-ethoxyethyl 4-[13-(4-chlorophenyl)-tridec-12-ynylamino]benzoate as a white solid.

EXAMPLE 41

Preparation of methyl 4-[13-(4-chlorophenyl)tridec-12-ynylamino]benzoate

A solution of 50.5 g. of 4-[13-(4-chlorophenyl)tridec-12-ynylamino]benzoic acid and 34.4 ml. of boron trifluoride etherate in 200 ml. of methanol is stirred under reflux for 44 hours, allowed to cool, and poured into 1.20 liters of ice-cold 5% aqueous sodium carbonate solution. The white solid is collected by filtration and recrystallized from benzene-ethanol to yield methyl 4-[13-(4-chlorophenyl)tridec-12-ynylamino]benzoate.

EXAMPLE 42

Preparation of 1-(methoxycarbonyl)propyl 4-[13-(4-chlorophenyl)tridec-12-ynylamino]benzoate To a solution of 10.0 g. 4-[13-(4-chlorophenyl)tridec-12-ynylamino]benzoyl chloride hydrochloride in 200 ml. methylene chloride added dropwise a solution of 3 g. methyl α-hydroxybutyrate and 5 g. triethylamine in 100 ml. ether. After 17 hours stirring at room temperature, the precipitate is collected and washed with several portions of ether. The ether solution is washed with water, dried and evaporated to yield 1-(methoxycarbonyl)propyl 4-[13-(4-chlorophenyl)tridec-12-ynylamino]benzoate as a white solid.

EXAMPLE 43

Preparation of 1-(ethoxycarbonyl)ethyl 4-[13-(4-chlorophenyl)tridec-12-ynylamino]benzoate To a warm mixture of 7 g. sodium 4-[13-(4-chlorophenyl)tridec-12-ynylamino]benzoate in 100 ml. ethanol is added 4.7 g. ethyl α-tosyloxypropionate. After 17 hours at reflux, the cooled solution is diluted with an equal volume of water and the resultant precipitate is filtered. After washing with cold ethanol and drying, the product is crystallized from acetonitrile to yield 1-(ethoxycarbonyl)ethyl 4-[13-(4-chlorophenyl)tridec-12-ynylamino]benzoate as colorless crystals.

EXAMPLE 44

Preparation of 1-carboxyethyl 4-[13-(4-chlorophenyl)tridec-12-ynylamino]benzoate A flask containing 10.0 g. 4-[13-(4-chlorophenyl)tridec-12-ynylamino]benzoic acid, 3.3 g. lactic acid, 500 mg. toluene sulfonic acid and 500 ml. toluene is equipped with a Soxhlet extractor charged with activated 4A Linde molecular sieves. The solution is refluxed for 24 hours during which time the Soxhlet extractor is charged twice more with fresh sieves. The hot solution is filtered and left to cool, whereupon 1-carboxyethyl 4-[13-(4-chlorophenyl)tridec-12-ynylamino]benzoate separates as off-white crystals.

EXAMPLE 45

Preparation of diethyl 0-{4-[13-(4-chlorophenyl)tridec-12-ynylamino]benzoyl}tartrate A mixture of 4-[N-trifluoroacetyl-13-(4-chlorophenyl)tridec-12-ynylamino]benzoyl chloride and 1.2 g. triethylamine in 100 ml. warm ether is treated with 2.5 g. diethyl tartrate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields diethyl 0-{4-[13-(4-chlorophenyl)tridec-12-ynylamino]benzoyl}tartrate as a white, crystalline solid.

EXAMPLE 46

Preparation of 0-{4-[13-(4-chlorophenyl)tridec-12-ynylamino]benzoyl}malic acid

A warm solution of 4-[N-carbobenzyloxy-13-(4-chlorophenyl)tridec-12-ynylamino]benzoyl chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered, and the solution is evaporated. The residue is crystallized from acetic acid to yield 0-{4-[13-(4-chlorophenyl)tridec-12-ynylamino]benzoyl}malic acid.

EXAMPLE 47

Preparation of 2-(ethoxycarbonyl)vinyl 4-[13-(4-chlorophenyl)tridec-12-ynylamino]benzoate To a mixture containing 4.3 g. 1-{4-[N-(t-butyloxycarbonyl)-13-(4-chlorophenyl)tridec-12-ynylamino]benzoyl}imidazole, 50 ml. 5N sodium hydroxide is added 3 g. ethyl α-formyl acetate. The solution is vigorously stirred for 24 hours. The layers are separated, and the chloroform solution is washed once with 50 ml. 1N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of 2-(ethoxycarbonyl)vinyl 4-[13-(4-chlorophenyl)tridec-12-ynylamino]benzoate.

EXAMPLE 48

Preparation of 1-{4-[13-(4-chlorophenyl)tridec-12-ynylamino]benzoyl}piperidine

To a chilled solution of 35 ml. of piperidine, 2.5 ml. of triethylamine and 0.6 g. of dimethylaminopyridine in 100 ml. of diethyl ether is added (½ hour) a solution of 8.3 g. of 4-[13-(4-chlorophenyl)tridec-12-ynylamino]benzoyl chloride hydrochloride in 50 ml. of ether. The solution is warmed to room temperature and maintained there for two hours. The solution is heated to reflux for an additional 2 hours at which time the reaction is complete. The solution is cooled, extracted twice with water and dried. The solvent is removed in vacuo and the solid is recrystallized from diethyl ether to yield 1-{4-[13-(4-chlorophenyl)tridec-12-ynylamino]benzoyl}piperidine.

EXAMPLE 49

Preparation of ethyl 4-[13-(4-chlorophenyl)tridec-12-ynylamino]hippurate

To a solution of 18.0 g. of 4-[13-(4-chlorophenyl)tridec-12-ynylamino]benzoic acid in a mixture of dioxane and methylene chloride is added gaseous hydrogen chloride for 10 minutes. The slurry is cooled and 18 ml. of thionyl chloride added. The slurry is brought to reflux for 2 hours and then concentrated under vacuum (thrice diluting with dioxane each time). The final amber solution is diluted with 100 ml. of dioxane and this solution added to freshly prepared ethyl glycinate in 300 ml. of methylene chloride containing 1 g. of dimethylaminopyridine and 10 ml. of triethylamine. After 16 hours at room temperature the reaction appeared complete but was refluxed for 2 hours, cooled and filtered. The mother liquor is extrated with water and 10% hydrochloric acid. The solution is dried and concentrated in vacuo to an amber liquid. A sample is pre-absorbed on silica and eluted with ether. Evaporation of the eluate yields a solid, which is recrystallized from acetonitrile to yield ethyl 4-[13-(4-chlorophenyl)tridec-12-ynylamino]hippurate as a white solid.

EXAMPLE 50

Preparation of N-{4-[13-(4-chlorophenyl)tridec-12-ynylamino]-benzoyl}glycine

A mixture of 26.4 g. of ethyl N-{4-[13-(4-chlorophenyl)tridec-12-ynylamino]benzoyl}glycinate, 110 ml. of 1N sodium hydroxide solution; and 100 ml. of ethanol is stirred at ambient temperature for 2 hours and then partially evaporated. The aqueous solution is washed with diethyl ether, acidified with 6N hydrochloric acid, and filtered. The white solid is dried in vacuo and recrystallized from acetone to yield N-{4-[13-(4-chlorophenyl)tridec-12-ynylamino]benzoyl}glycine.

EXAMPLE 51

Preparation of 4-[13-(4-chlorophenyl)tridec-12-ynylamino]-N-(phenylsulfonyl)benzamide A solution of 31.4 g. of benzenesulfonamide in 250 ml. of dry dimethylacetamide is added dropwise, with stirring and cooling, to a suspension of 5.5 g. of sodium hydride in 100 ml. of dry dimethylacetamide during 30 minutes at room temperature. Stirring is continued for a further 30 minutes. In the meantime, a mixture of 36.5 g. of 4-[13-(4-chlorophenyl)tridec-12-ynylamino]benzoic acid in 100 ml. of methylene chloride, 300 ml. of dimethoxyethane, and 40 ml. of thionyl chloride is refluxed for 1 hour and 15 minutes. The solution is evaporated and to the resulting oil residue is added, in one portion, the previously prepared mixture of sodium benzenesulfonamide in dimethylacetamide. The mixture is stirred for 30 minutes, without cooling, and then filtered. The filtrate is poured into 2 l. of water and 250 ml. of saturated sodium chloride solution. The product is collected by filtration and then dissolved in methylene chloride, the mixture is filtered through diatomaceous earth, and brine is added to break the emulsion. The layers are separated, the organic phase is dried and evaporated. The residue is crystallized from toluene to yield 4-[13-(4-chlorophenyl)tridec-12-ynylamino]-N-(phenylsulfonyl)benzamide.

EXAMPLE 52

Preparation of N-{4-[13-(4-chlorophenyl)tridec-12-ynylamino]benzoyl}methanesulfonamide A solution of 25.2 g. of 4-[13-(4-chlorophenyl)tridec-12-ynylamino]benzoyl chloride hydrochloride and 5.6 g. of methanesulfonamide in 250 ml. of pyridine is stirred under reflux for 2 hours and then concentrated in vacuo. The residue is partitioned between water and diethyl ether; the aqueous layer acidified with 1 N HCl, and the organic layer separated, dried and evaporated. Crystallization of the residual white solid from 60% aqueous acetic acid and then from methylene chloride-hexane affords N-{4-[13-(4-chlorophenyl)tridec-12-ynylamino]benzoyl}methanesulfonamide as a white solid.

EXAMPLE 53

Preparation of N-{4-[13-(4-chlorophenyl)tridec-12-ynylamino]benzoyl}alanine

A solution of 4.75 g. of 4-[N-trifluoroacetyl-13-(4-chlorophenyl)tridec-12-ynylamino]benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the N-{4-[13-(4-chlorophenyl)tridec-12-ynylamino]benzoyl}alanine as a white, crystalline solid.

EXAMPLE 54

Preparation of N-{4-[13-(4-chlorophenyl)tridec-12-ynylamino]benzoyl}benzamide

One gram of a 50% oil dispersion of sodium hydride is washed with petroleum ether by decantation, dried, and suspended in 5 ml. of tetrahydrofuran. To this stirred mixture is added a solution of 2.42 g. of benzamide in 5 ml. of tetrahydrofuran in one portion. An initial hydrogen evolution is observed. While stirring (30 min.), the sodium hydride gradually disappears and a white, milky, turbid mixture forms. A solution of 0.9 g. of 4-[N-trifluoroacetyl-13-(4-chlorophenyl)tridec-12-ynylamino]benzoyl chloride in 3 ml. of tetrahydrofuran is added dropwise during 5 minutes to the mixture. The whole milky mixture is stirred at room temperature under nitrogen for one hour. The mixture is then poured into water and extracted with ether. The ether extract is washed with water and brine and dried over sodium sulfate. Evaporation of the solvent affords a pale yellow solid. The solid is recrystallized from ether/acetonitrile (50/50) and then from acetonitrile to yield N-{4-[13-(4-chlorophenyl)tridec-12-ynylamino]benzoyl}benzamide.

EXAMPLE 55

Preparation of
N-{4-[13-(4-chlorophenyl)tridec-12-ynylamino]benzoyl}piperidine

To a warm solution of 4-[N-carbobenzoyloxy-13-(4-chlorophenyl)tridec-12-ynylamino]benzoyl chloride and 1.3 g. of triethylamine in 100 ml. ether is added 1.2 g. of piperidine. An immediate precipitate forms, the mixture is refluxed for one hour and then filtered. The solid is extracted several times with hot ether and the ether is evaporated to yield a white solid. The solid is dissolved in tetrahydrofuran (100 ml.) and hydrogenated over 600 mg. 10% palladium-on-carbon at 50 psi until hydrogen uptake stops. The catalyst is filtered and the filtrate evaporated. The residue is crystallized from acetic acid to yield N-{4-[13-(4-chlorophenyl)tridec-12-ynylamino]benzoyl}piperidine as a crystalline mass.

EXAMPLE 56

Preparation of
N-(2,3-dihydroxypropyl)-4-[13-(4-chlorophenyl)tridec-12-ynylamino]benzamide To a mixture containing 4.3 g. of 1-{4-(tert-butyloxycarbonyl)-4-[13-(4-chlorophenyl)tridec-12-ynylamino]benzoyl}imidazole, 50 ml. of chloroform, and 50 ml. of 5N sodium hydroxide is added 1.1 g. of 3-amino-1,2-propanediol. The solution is vigorously stirred for 24 hours, the layers are separated, and the chloroform solution is washed once with 50 ml. of 1 N sodium hydroxide. The solvent is evaporated and the residue is heated for 30 minutes at 40° C. in 50 ml. of anhydrous trifluoroacetic acid. The solvent is again evaporated and the oil is crystallized from acetone to yield light yellow crystals of N-(2,3-dihydroxypropyl)-4-[13-(4-chlorophenyl)tridec-12-ynylamino]benzamide.

EXAMPLE 57

Preparation of diethyl
4-[13-(4-chlorophenyl)tridec-12-ynylamino]benzoylmalonate A solution of 26.6 g. of diethyl malonate and 10 ml. of 1,2-dimethoxyethane is added to a suspension of 4.0 g. of sodium hydride in 1,2-dimethoxyethane under argon. A solution of 17.3 g. of 1,2-dimethoxyethane is then added. The reaction mixture is refluxed for 4.5 hours, cooled, poured on ice, acidified, and extracted with ether. The ether solution is washed with water and saturated sodium chloride solution, dried over anhydrous sodium sulfate and concentrated to dryness. Addition of a small amount of ethanol to the residue gives a solid which is filtered and discarded. The ethanol filtrate is concentrated and the residue is recrystallized from ether to yield diethyl 4-[13-(4-chlorophenyl)tridec-12-ynylamino]benzoylmalonate.

EXAMPLE 58

Preparation of tert-butyl ethyl
4-[13-(4-chlorophenyl)tridec-12-ynylamino]benzoylmalonate A solution of 28.0 g. of tert-butyl ethyl malonate in 10 ml. of 1,2-dimethoxyethane is added to a suspension of 4.0 g. of sodium hydride in 1,2-dimethoxyethane under argon. A solution of 17.3 g. of 4-[13-(4-chlorophenyl)tridec-12-ynylamino]benzoyl chloride hydrochloride in 1.2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. The residue is then recrystallized from ether to yield tert-butyl ethyl 4-[13-(4-chlorophenyl)tridec-12-ynylamino]benzoyl malonate.

EXAMPLE 59

Preparation of ethyl
2-{4-[13-(4-chlorophenyl)tridec-12-ynylamino]benzoyl}acetoacetate A solution of 21.6 g. of ethyl acetoacetate and 10 ml. of 1,2-dimethoxyethane is added to a suspension of 4.0 g. of sodium hydride in 1,2-dimethoxyethane under argon. A solution of 17.3 g. of 4-[13-(4-chlorophenyl)-tridec-12-ynylamino]benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. Recrystallization from ether affords ethyl 2-{4-[13-(4-chlorophenyl)tridec-12-ynylamino]benzoyl}acetoacetate as a white solid.

EXAMPLE 60

Preparation of ethyl
4-[13-(4-chlorophenyl)tridec-12-ynylamino]benzoyl acetate

A solution of 3.0 g. of tert-butyl ethyl 4-[13-(4-chlorophenyl)tridec-12-ynylamino]benzoylmalonate 10 ml. of trifluoroacetic acid is warmed with stirring for 3 hours. The solution is poured onto ice and neutralized with potassium hydroxide. The resulting precipitate is collected by filtration, washed with water and dried. Recrystallization from chloroform affords ethyl 4-[13-(4-chlorophenyl)tridec-12-ynylamino]benzoylacetate.

EXAMPLE 61

Preparation of 4-[13-(4-chlorophenyl)tridec-12-ynylamino]benzoyl acetic acid

Two grams of ethyl
4-[13-(4-chlorophenyl)tridec-12-ynylamino]benzoylacetate is added to a solution of potassium hydroxide in 50 ml. of 1:9 water-ethanol. The reaction mixture is stirred for 24 hours at room temperature. Careful neutralization with sulfuric acid gave a precipitate which is filtered, washed with water, and dried to yield 4-[13-(4-chlorophenyl)tridec -12-ynylamino]benzoylacetic acid.

EXAMPLE 62

Preparation of
4'-[13-(4-chlorophenyl)tridec-12-ynylamino]-2-(methylsulfinyl)acetophenone To a solution of 5.8 g. of dimethyl sulfoxide, dried over sieves, and 50 ml. of tetrahydrofuran is slowly added 28 ml. of n-butyllithium (2.4 M in hexane). To this mixture is added 10 g. of methyl 4-[13-(4-chlorophenyl)tridec-12-ynylamino]benzoate in 200 ml. of tetrahydrofuran. After two hours, the reaction mixture is poured onto ice, acidified with dilute hydrochloric acid and quickly extracted with chloroform. The chloroform extract is washed with water and saturated sodium chloride solution, and dried over anhydrous sodium sulfate. Concentration affords a solid which is washed with 500 ml. of hot hexane, filtered while hot and then washed with hexane. The white solid is dried in vacuo to yield 4'-[13-(4-chlorophenyl)tridec-12-ynylamino]-2-(methylsulfinyl)acetophenone.

EXAMPLE 63

Preparation of 4'-[13-(4-chlorophenyl)tridec-12-ynylamino]-2-(phenylsulfonyl)acetophenone A solution of 864 mg. of sodium hydride and 5.3 g. of methylphenylsulfone in 20 ml. of 1,2-dimethoxyethane is stirred at 60° C. for one hour under an atmosphere of argon. To this solution is added a solution of 5.0 g. of methyl 4-[13-(4-chlorophenyl)tridec-12-ynylamino]benzoate in 50 ml. of tetrahydrofuran and the reaction mixture is stirred at 60° C. for 1.5 hours. The mixture is cooled, poured onto ice, acidified with dilute hydrochloric acid to pH 3 and then extracted with chloroform. The organic layer is separated, washed with water and saturated sodium chloride solution, dried over anhydrous sodium sulfate and then concentrated to dryness. The crude solid is chromatographed on silica gel, eluting with methylene chloride to yield 4'-[13-(4-chlorophenyl)tridec-12-ynylamino]-2-(phenylsulfonyl)acetophenone.

EXAMPLE 64

Preparation of 4'-[13-(4-chlorophenyl)tridec-12-ynylamino]-2-phenylsulfinyl)acetophenone To a solution of 6.2 g. of methylphenylsulfoxide, dried over sieves, and 50 ml. of tetrahydrofuran is slowly added 28 ml. of n-butyllithium (2,4 M in hexane). To this mixture is added 10 g. of a solution of methyl 4-[13-(4-chlorophenyl)tridec-12-ynyl-amino]benzoate in 200 ml. of tetrahydrofuran. After two hours, the reaction mixture is poured into ice, acidified with diluted hydrochloric acid and quickly extracted with chloroform. The chloroform layer is washed with water and saturated sodium chloride solution and dried over anhydrous sodium sulfate. Concentration affords a solid which is washed with 500 ml. of hot hexane, filtered while hot, and then washed with 50 ml. of hexane. The white solid is dried in vacuo yielding 4'-[13-(4-chlorophenyl)tridec-12-ynylamino]-2-(phenylsulfinyl)acetophenone.

EXAMPLE 65

Preparation of 3-{4'-[13-(4-chlorophenyl)tridec-12-ynylamino]benzoyl}-2,4-pentanedione A solution of 28.4 g. of 2,4-pentanedione and 20 ml. of 1,2-dimethoxyethane is added to a suspension of 13.6 g. of sodium hydride in 220 ml. of 1,2-dimethoxyethane under argon. A solution of 28.7 g. of 4-[13-(4-chlorophenyl)tridec-12-ynylamino]benzoyl chloride hydrochloride in 1,2-dimethoxyethane is then added. The reaction mixture is stirred at room temperature for 12 hours, cooled, poured on ice and extracted with ether. The ether solution is washed with water and saturated sodium chloride solution, dried over anhydrous sodium sulfate and concentrated. The residue is then chromatographed over silica gel to yield 3-{4'-[13-(4-chlorophenyl)tridec-12-ynylamino]benzoyl} 2,4-pentanedione.

EXAMPLE 66

Preparation of methyl 3-{4-[13-(4-chlorophenyl)tridec-12-ynylamino]benzoyl}propionate A mixture of 35 g. of 3-(4-acetamidobenzoyl)propionic acid, 700 ml. of methanol and 1.4 ml. of concentrated sulfuric acid is refluxed for 76 hours. The solution is cooled to 35° C. and poured onto 7 g. of anhydrous sodium acetate while stirring. The reaction mixture is stirred in an ice-bath. The solid is collected and washed with cold methanol to yield methyl 3-(4-aminobenzoyl)priopionate as a white solid. A mixture of this solid, 9.2 g. of 13-(4-chlorophenyl)tridec-12-ynyl bromide and 4.2 g. of potassium carbonate is stirred for 20 hours at 125° C. under nitrogen. The mixture is then cooled to 25° C. and 30 ml. of water is added. After stirring, the product is filtered and washed with water. Recrystallization from methanol affords methyl 3-{4-[13-(4-chlorophenyl)tridec-12-ynylamino]benzoyl}propionate as a white solid.

EXAMPLE 67

Preparation of 3-{4-[13-(4-chlorophenyl)tridec-12-ynylamino]benzoyl}propionic acid A solution of 5.4 g. of methyl 3-{4-[13-(4-chlorophenyl)tricdec-12-ynylamino]benzoyl}propionate is stirred with 5.4 g. of potassium hydroxide in 100 ml. of 95% ethanol for 3 hours at reflux. The reaction mixture is cooled, diluted with 50 ml. of ethanol and 100 ml. of water, neutralized with hydrochloric acid. The solution is cooled to room temperature and filtered. The white solid is washed with 50% aqueous ethanol and dried. The product is recrystallized from ethanol to yield 3-{4-[13-(4-chlorophenyl)tridec-12-ynylamino]benzoy}propionic acid as a white crystalline solid.

TABLE I

The following terminal acetylenic compounds are prepared following the method of Example 1, using the appropriate aldehyde.

| Example No. | Aldehyde | Aryl or Heteroaryl Acetylenic Compound |
| --- | --- | --- |
| 68 | 2,4-Dichlorobenzaldehyde | 2,4-Dichlorophenylacetylene |
| 69 | 4-Methoxybenzaldehyde | |
| | 4-Methoxyphenylacetylene | |
| 70 | 3-(2-Pyridyl)propionaldehyde | 4-(2-Pyridyl)-4-butyne |
| 71 | 3-(2-Furyl)propionaldehyde | 4-(2-Furyl)-4-butyne |
| 72 | 2-Chloro-6-fluorobenzaldehyde | 2-Chloro-6-fluorophenylacetylene |
| 73 | 5-Methylfurfuryl | 2-Ethynyl-5-methylfuran |
| 74 | 4-Chlorophenylacetaldehyde | 3-(4-Chlorophenyl)-1-propyne |
| 75 | 2-Methyl-3-(4-chlorophenyl)-propionaldehyde | 3-Methyl-4-(4-chlorophenyl)-1-butyne |

TABLE I-continued

The following terminal acetylenic compounds are prepared following the method of Example 1, using the appropriate aldehyde.

| Example No. | Aldehyde | Aryl or Heteroaryl Acetylenic Compound |
|---|---|---|
| 76 | 4-Methoxyphenylacetaldehyde | 3-(4-Methoxyphenyl)-1-propyne |
| 77 | 4-Methoxyhydrocinnamaldehyde | 4-(4-Methoxyphenyl)-1-butyne |
| 78 | 4-(2-Pyridyl)butyraldehyde | 5-(2-Pyridyl)-1-pentyne |
| 79 | 4-(6-Methyl-2-pyridyl)butyraldehyde | 5-(6-Methyl-2-pyridyl)-1-pentyne |
| 80 | 2-Furylacetaldehyde | 3-(2-Furyl)-1-propyne |
| 81 | 5-Ethyl-2-furaldehyde | 5-Methyl-2-ethynylfuran |

TABLE II

The following aryl- or heteroarylalkynyl bromides are prepared by the method of Example 5. The required ω-bromoalkyl toluene sulfonates are prepared by the method of Examples 2, 3 and 4.

| Example No. | Acetylene | Bromoalkyl tosylate | Aryl- or Heteroarylalkynyl Bromide |
|---|---|---|---|
| 82 | 2-Chloro-6-fluorophenyl acetylene | 9-Bromononyl tosylate | 11-(2-Chloro-6-fluorophenyl)undec-10-ynyl bromide |
| 83 | 3,4-Dichloropentylacetylene | 11-Bromoundecyl tosylate | 13-(3,4-Dichlorophenyl)tridec-12-ynyl-bromide |
| 84 | 4-Chlorphenylacetylene | 7-Bromoheptyl tosylate | 9-(4-Chlorophenyl)non-8-ynyl bromide |
| 85 | 4-Chlorophenylacetylene | 15-Bromopentadecyl tosylate | 17-(4-Chlorophenyl)heptadec-16-ynyl-bromide |
| 86 | 4-Methoxyphenylacetylene | 5-Bromopentyl tosylate | 7-(4-Methoxyphenyl)hept-6-ynyl bromide |
| 87 | 4-Fluorophenylacetylene | 10-Bromodecyl tosylate | 12-(4-Fluorophenyl)dodec-11-ynyl-bromide |
| 88 | 3-Methylphenylacetylene | 6-Bromohexyl tosylate | 8-(3-,Methylphenyl)oct-7-ynyl bromide |
| 89 | Pentafluorophenylacetylene | 14-Bromotetradecyl tosylate | 16-(Pentafluorophenyl)hexadec-15-ynyl-bromide |
| 90 | 4-Phenyl-1-butyne | 8-Bromooctyl tosylate | 12-Phenyldodec-9-ynylbromide |
| 91 | 5-Phenyl-1-pentyne | 4-Bromobutyl tosylate | 9-Phenylnon-5-ynylbromide |
| 92 | 5-Phenyl-1-pentyne | 11-Bromoundecyl tosylate | 16-Phenylhexadec-12-ynylbromide |
| 93 | 3-(3-Methylphenyl)-1-propyne | 9-Bromononyl tosylate | 12-(3-Methylphenyl)dodec-10-ynyl bromide |
| 94 | 3-(4-Methoxyphenyl)-1-propyne | 9-Bromononyl tosylate | 12-(4-Methoxyphenyl)dodec-10-ynyl bromide |
| 95 | 4-(4-Methoxyphenyl)-1-butyne | 3-Bromopropyl tosylate | 7-(4-Methoxyphenyl)hept-4-ynyl bromide |
| 96 | 3-Methyl-4-(4-chlorophenyl)-1-butyne | 4-Bromobutyl tosylate | 8-(4-Chlorophenyl)-7-methyloct-5-ynyl bromide |
| 97 | 3-Methyl-4-(4-chlorophenyl)-1-butyne | 14-Bromotetradecyl tosylate | 18-(4-Chlorophenyl)-17-methyloctadec-15-ynyl bromide |
| 98 | 4-Bromophenylacetylene | 13-Bromodecyl tosylate | 15-(4-Bromophenyl)-pentadec-14-ynyl bromide |
| 99 | 6-Phenyl-1-hexyne | 7-Bromoheptyl tosylate | 13-phenyltridec-8-ynyl bromide |
| 100 | 4-Chlorophenylacetylene | 4-Bromobutyl tosylate | 6-(4-Chlorophenyl)hex-5-ynyl bromide |
| 101 | 4-Chlorophenylacetylene | 16-Bromohexadecyl tosylate | 18-(4-Chlorphenyl)octadec-17-ynyl bromide |
| 102 | Phenylacetylene | 5-Bromopentyl tosylate | 7-Phenylhept-6-ynyl bromide |
| 103 | Phenylacetylene | 12-Bromododecyl tosylate | 14-Phenyltetradec-13-ynyl bromide |
| 104 | 4-(4-Propyl)phenylacetylene | 8-Bromooctyl tosylate | 10-[4-(2-Propyl)phenyl]dec-9-ynyl bromide |
| 105 | 2-Ethynylthiophene | 11-Bromoundecyl tosylate | 13-(2-Thienyl)tridec-12-ynyl bromide |
| 106 | 2-Ethynylfuran | 6-Bromohexyl tosylate | 8-(2-Furyl)oct-7-ynyl bromide |
| 107 | 2-Ethynylpyridine | 4-Bromobutyl tosylate | 6-(2-Pyridyl)hex-5-ynyl bromide |
| 108 | 5-Ethyl-2-ethynylfuran | 5-Bromopentyl tosylate | 7-(5-Ethyl-2-furyl)hept-6-ynyl bromide |
| 109 | 3-(2-Furyl)-1-propyne | 10-Bromodecyl tosylate | 13-(2-Furyl)tridec-11-ynyl bromide |
| 110 | 5-(2-Pyridyl)-1-pentyne | 4-Bromobutyl tosylate | 9-(2-pyridyl)non-5-ynyl bromide |
| 111 | 5-(6-Methyl-2-pyridyl)-1-pentyne | 12-Bromododecyl tosylate | 17-(6-Methyl-2-pyridyl)heptadec-13-ynyl bromide |
| 112 | 5-Methyl-2-ethynylthiophene | 8-Bromooctyl tosylate | 10-(5-Methyl-2-thienyl)dec-9-ynyl bromide |

TABLE III

The following ω-aryl- or heteroaryl-3-alkynyl alcohols are prepared by the method of Example 8 from the appropriate acetylenes.

| Example No. | Acetylene | Aryl- or Heteroaryl Alcohol |
|---|---|---|
| 113 | 3-(4-Chlorophenyl)-1-propyne | 5-(4-Chlorophenyl)pent-3-ynyl alcohol |

TABLE III-continued

The following ω-aryl- or heteroaryl-3-alkynyl alcohols are prepared by the method of Example 8 from the appropriate acetylenes.

| Example No. | Acetylene | Aryl- or Heteroaryl Alcohol |
|---|---|---|
| 114 | 4-(4-Methoxyphenyl)-1-butyne | 6-(4-Methoxyphenyl)hex-3-ynyl alcohol |
| 115 | 3-Methylphenylacetylene | 4-(3-Methylphenyl)but-3-ynyl alcohol |
| 116 | 2-Pyridylacetylene | 4-(2-Pyridyl)but-3-ynyl alcohol |
| 117 | 5-Phenyl-1-pentyne | 7-Phenylhept-3-ynyl alcohol |
| 118 | 4-Chlorophenylacetylene | 4-(4-Chlorophenyl)but-3-ynyl alcohol |
| 119 | Phenylacetylene | 4-Phenylbut-3-ynyl alcohol |
| 120 | 3-(2-Thienyl)-1-propyne | 5-(2-Thienyl)pent-3-ynyl alcohol |
| 121 | (2-Furyl)acetylene | 4-(2-Furyl)but-3-ynyl alcohol |
| 122 | Pentafluorophenylacetylene | 4-(Pentafluorophenyl)but-3-ynyl alcohol |

TABLE IV

The following ethyl 4-(aryl- or heteroarylalkynylamino)benzoates are preapred by the methods of Examples 6 or 10. The methanesulfonates required are prepared as described in Example 9.

| Example No. | 4-(Aryl- or heteroarylalkynylamino)benzoate |
|---|---|
| 123 | Ethyl 4-[11-(2-chloro-6-fluorphenyl)undec-10-ynylamino]benzoate |
| 124 | Ethyl 4-[13-(3,4-dichlorophenyl)tridec-12-ynylamino]benzoate |
| 125 | Ethyl 4-[9-(4-chlorophenyl)non-8-ynylamino]benzoate |
| 126 | Ethyl 4-[17-(4-chlorophenyl)heptadec-16-ynylamino]benzoate |
| 127 | Ethyl 4-[7-(4-methoxyphenyl)hept-6-ynylamino]benzoate |
| 128 | Ethyl 4-[12-(4-fluorophenyl)dodec-11-ynylamino]benzoate |
| 129 | Ethyl 4-[8-(3-methylphenyl)oct-7-ynylamino]benzoate |
| 130 | Ethyl 4-[16-(pentafluorophenyl)hexadec-15-ynylamino]benzoate |
| 131 | Ethyl 4-(12-phenyldodec-9-ynylamino)benzoate |
| 132 | Ethyl 4-(9-phenylnon-5-ynylamino)benzoate |
| 133 | Ethyl 4-(16-phenylhexadec-12-ynylamino)benzoate |
| 134 | Ethyl 4-[12-(3-methylphenyl)dodec-10-ynylamino]benzoate |
| 135 | Ethyl 4-[12-(4-methoxyphenyl)dodec-10-ynylamino]benzoate |
| 136 | Ethyl 4-[7-(4-methoxyphenyl)hept-4-ynylamino]benzoate |
| 137 | Ethyl 4-[8-(4-chlorophenyl)-7-methyloct-5-ynylamino]benzoate |
| 138 | Ethyl 4-[18-(4-chlorophenyl)-17-methyloctadec-15-ynylamino]benzoate |
| 139 | Ethyl 4-[15-(4-bromophenyl)pentadec-14-ynylamino]benzoate |
| 140 | Ethyl 4-(13-phenyltridec-8-ynylamino)benzoate |
| 141 | Ethyl 4-[6-(4-chlorophenyl)hex-5-ynylamino]benzoate |
| 142 | Ethyl 4-[18-(4-chlorophenyl)octadec-17-ynylamino]benzoate |
| 143 | Ethyl 4-(7-phenylhept-6-ynylamino)benzoate |
| 144 | Ethyl 4-(14-phenyltetradec-13-ynylamino)benzoate |
| 145 | Ethyl 4-{10-[4-(2-propyl)phenyl]dec-9-ynylamino}benzoate |
| 146 | Ethyl 4-[13-(2-thienyl)tridec-12-ynylamino]benzoate |
| 147 | Ethyl 4-[8-(2-furyl)oct-7-ynylamino]benzoate |
| 148 | Ethyl 4-[6-(2-pyridyl)hex-5-ynylamino]benzoate |
| 149 | Ethyl 4-[7-(5-ethyl-2-furyl)hept-6-ynylamino]benzoate |
| 150 | Ethyl 4-[13-(2-furyl)tridec-11-ynylamino]benzoate |
| 151 | Ethyl 4-[9-(2-pyridyl)non-5-ynylamino]benzoate |
| 152 | Ethyl 4-[17-(6-methyl-2-pyridyl)heptadec-13-ynylamino]benzoate |
| 153 | Ethyl 4-[10-(5-methyl-2-thienyl)dec-9-ynylamino]benzoate |
| 154 | Ethyl 4-[5-(4-chlorophenyl)pent-3-ynylamino]benzoate |
| 155 | Ethyl 4-[6-(4-methoxyphenyl)hex-3-ynylamino]benzoate |
| 156 | Ethyl 4-[4-(3-methylphenyl)but-3-ynylamino]benzoate |
| 157 | Ethyl 4-[4-(2-pyridyl)but-3-ynylamino]benzoate |
| 158 | Ethyl 4-(7-phenylhept-3-ynylamino)benzoate |
| 159 | Ethyl 4-[4-(4-chlorophenyl)but-3-ynylamino]benzoate |
| 160 | Ethyl 4-(4-phenylbut-3-ynylamino)benzoate |
| 161 | Ethyl 4-[5-(3-thienyl)pent-3-ynylamino]benzoate |
| 162 | Ethyl 4-(4-furylbut-3-ynylamino)benzoate |
| 163 | Ethyl 4-[4-(pentafluorophenyl)but-3-ynylamino]benzoate |

TABLE V

The following 4-(aryl- or heteroarylalkynylamino)benzoic acids are prepared from esters of Table IV by the method of Example 7.

| Example No. | 4-(Aryl- or heteroarylalkynylamino)benzoic acid |
|---|---|
| 164 | 4-[11-(2-Chloro-6-fluorophenyl)undec-10-ynylamino]benzoic acid |
| 165 | 4-[13-(3,4-Dichlorophenyl)tridec-12-ynylamino]benzoic acid |
| 166 | 4-[9-(4-Chlorophenyl)non-8-ynylamino]benzoic acid |
| 167 | 4-[17-(4-Chlorphenyl)heptadec-16-ynylamino]benzoic acid |
| 168 | 4-[7-(4-Methoxyphenyl)hept-6-ynylamino]benzoic acid |
| 169 | 4-[12-(4-Fluorophenyl)dodec-11-ynylamino]benzoic acid |
| 170 | 4-[8-(3-Methylphenyl)oct-7-ynylamino]benzoic acid |
| 171 | 4-[16-(Pentafluorophenyl)hexadec-15-ynylamino]benzoic acid |
| 172 | 4-(12-Phenyldodec-9-ynylamino)benzoic acid |
| 173 | 4-(9-Phenylnon-5-ynylamino)benzoic acid |
| 174 | 4-(16-Phenylhexadec-12-ynylamino)benzoic acid |
| 175 | 4-[12-(3-Methylphenyl)dodec-10-ynylamino]benzoic acid |

TABLE V-continued

The following 4-(aryl- or heteroarylalkynylamino)benzoic acids are prepared from esters of Table IV by the method of Example 7.

| Example No. | 4-(Aryl- or heteroarylalkynylamino)benzoic acid |
|---|---|
| 176 | 4-[12-(4-Methoxyphenyl)dodec-10-ynylamino]benzoic acid |
| 177 | 4-[7-(4-Methoxyphenyl)hept-4-ynylamino]benzoic acid |
| 178 | 4-[8-(4-Chlorophenyl)-7-methyloct-5-ynylamino]benzoic acid |
| 179 | 4-[18-(4-Chlorophenyl)-17-methyloctadec-15-ynylamino]benzoic acid |
| 180 | 4-[15-(4-Bromophenyl)pentadec-14-ynylamino]benzoic acid |
| 181 | 4-(13-Phenyltridec-8-ynylamino)benzoic acid |
| 182 | 4-[6-(4-Chlorophenyl)hex-5-ynylamino]benzoic acid |
| 183 | 4-[18-(4-Chlorophenyl)octadec-17-ynylamino]benzoic acid |
| 184 | 4-(7-Phenylhept-6-ynylamino)benzoic acid |
| 185 | 4-(14-Phenyltetradec-13-ynylamino)benzoic acid |
| 186 | 4-{10-[4-(2-Propyl)phenyl]dec-9-ynylamino}benzoic acid |
| 187 | 4-[13-(2-Thienyl)tridec-12-ynylamino]benzoic acid |
| 188 | 4-[8-(2-Furyl)oct-7-ynylamino]benzoic acid |
| 189 | 4-[6-(2-Pyridyl)hex-5-ynylamino]benzoic acid |
| 190 | 4-[7-(5-Ethyl-2-furyl)hept-6-ynylamino]benzoic acid |
| 191 | 4-[13-(2-Furyl)tridec-11-ynylamino]benzoic acid |
| 192 | 4-[9-(2-Pyridyl)non-5-ynylamino]benzoic acid |
| 193 | 4-[17-(6-Methyl-2-pyridyl)heptadec-13-ynylamino]benzoic acid |
| 194 | 4-[10-(5-Methyl-2-thienyl)dec-9-ynylamino]benzoic acid |
| 195 | 4-[5-(4-Chlorophenyl)pent-3-ynylamino]benzoic acid |
| 196 | 4-[6-(4-Methoxyphenyl)hex-3-ynylamino]benzoic acid |
| 197 | 4-[4-(3-Methylphenyl)but-3-ynylamino]benzoic acid |
| 198 | 4-[4-(2-Pyridyl)but-3-ynylamino]benzoic acid |
| 199 | 4-(7-Phenylhept-3-ynylamino)benzoic acid |
| 200 | 4-[4-(4-Chlorophenyl)but-3-ynylamino]benzoic acid |
| 201 | 4-(4-Phenylbut-3-ynylamino)benzoic acid |
| 202 | 4-[5-(2-Thienyl)pent-3-ynylamino]benzoic acid |
| 203 | 4-[4-(2-Furyl)but-3-ynylamino]benzoic acid |
| 204 | 4-[4-(Pentafluorophenyl)but-3-ynylamino]benzoic acid |

TABLE VI

The following aryl- or heteroarylalkenyl halides or alcohols are prepared from the aldehydes or esters shown by the methods listed in the Table. The requisite aldehydes are prepared by the method of Example 12 and the requisite phosphonium salts are obtained by the method of Example 16.

| Example No. | Method of Example | Starting Material | Aryl- or Heteroarylalkenyl halide or alcohol |
|---|---|---|---|
| 205 | 18, 17 | 4-Chlorobenzaldehyde | 10-(4-Chlorophenyl)dec-9-enyl alcohol |
| 206 | 18, 17 | Phenylacetaldehyde | 6-Phenylhex-4-enyl alcohol |
| 207 | 18, 17 | Phenylacetaldehyde | 15-Phenylpentadec-13-enyl alcohol |
| 208 | 18, 17 | 2-Methylcinnamaldehyde | 9-Phenylnona-6,8-dienyl alcohol |
| 209 | 18, 17 | 2-Phenylpropionaldehyde | 5-Methyl-5-phenylpent-3-enyl alcohol |
| 210 | 18, 17 | 2-Phenylpropionaldehyde | 18-Methyl-18-phenyloctadec-16-enyl alcohol |
| 211 | 18, 17 | 4-Fluorobenzaldehyde | 11-(4-Fluorphenyl)undec-10-enyl alcohol |
| 212 | 18, 17 | 3-Bromobenzaldehyde | 7-(3-Bromophenyl)hept-6-enyl alcohol |
| 213 | 18, 17 | 2-Thiophenecarboxaldehyde | 10-(2-Thienyl)dec-9-enyl alcohol |
| 214 | 18, 17 | 2-Pyridinecarboxaldehyde | 13-(2-Pyridyl)tridec-12-enyl alcohol |
| 215 | 18, 17 | Indole-3-carboxaldehyde | 12-(3-indoyl)dodec-11-enyl alcohol |
| 216 | 24 | Methylcinnamate | Cinnamyl alcohol |
| 217 | 24 | Methyl 4-fluorocinnamate | 4-Fluorocinnamyl alcohol |
| 218 | 24 | Methyl 3-(trifluoromethyl)-cinnamate | 3-(Trifluoromethyl)cinnamyl alcohol |
| 219 | 21, 22 | 4,8-Dimethyl-3,7-nonadieno-nitrile | 2-(3,7-Dimethyl-2,6-octadienyl)-4-chloro-methylimidazole hydrochloride |
| 220 | 24 | Ethyl 5-octyl-2-thienyl-acrylate | 3-[(5-Octyl)-2-thienyl]prop-2-ene-1-ol |
| 221 | 15, 17 | 2-Ethylthiophene | 9-[2-(5-Ethyl)thienyl]non-8-ene-1-ol |
| 222 | 18, 17 | 5-Methylfurfural | 15-[2-(5-Methyl)furyl]pentadec-14-ene-1-ol |

TABLE VII

The following aryl- or heteroarylalkyl halides or alcohols are prepared from the appropriate starting materials by the methods shown. The requisite aryl - or heteroarylalkyl bromides are prepared by the method of Example 2. Saturated acids are prepared from the corresponding unsaturated acids by method of Example 19.

| Example No. | Method of Example(s) | Starting Material | Aryl- or Heteroarylalkyl halide or alcohol |
|---|---|---|---|
| 223 | 17 | 4-Chlorocinnamic acid | 3-(4-Chlorophenyl)propanol |
| 224 | 26 | 3-(4-Chlorophenyl)propyl-bromide and 1,10-dibromodecane | 13-(4-Chlorophenyl)tridecyl bromide |
| 225 | 26 | 4-(4-Methoxyphenyl)butyl-bromide and 1,6-dibromodecane | 10-(4-Methoxyphenyl)decyl bromide |
| 226 | 17 | Ethyl 3-[(5-octyl)-2-thienyl]acrylate | 3-[(5-Octyl)-2-thienyl]propanol |
| 227 | 26 | 4-Decyloxybenzyl bromide | 12-(4-Decyloxyphenyl)dodecyl bromide |

TABLE VII-continued

The following aryl- or heteroarylalkyl halides or alcohols are prepared from the appropriate starting materials by the methods shown. The requisite aryl - or heteroarylalkyl bromides are prepared by the method of Example 2. Saturated acids are prepared from the corresponding unsaturated acids by method of Example 19.

| Example No. | Method of Example(s) | Starting Material | Aryl- or Heteroarylalkyl halide or alcohol |
|---|---|---|---|
| 228 | 26 | 1-Bromoethylnaphthalene and 1,11-Dibromoundecane | 8-(1-Naphthyl)octyl bromide |
| 229 | 26 | 4-Benzyloxyphenethyl bromide and 1,6-dibromodecane | 14-(4-Benzyloxyphenyl)tetradecyl bromide |
| 230 | 21, 22 | Benzyl cyanide and 1,12-dibromododecane | 2-Benzyl-4-chloromethylimidazole hydrochloride |
| 231 | 21, 22 | Cycloheptyl cyanide | 2-Cycloheptyl-4-chloromethylimidazole hydrochloride |
| 232 | 21,22 | Butyronitrile | 2-propyl-4-chloromethylimidazole hydrochloride |
| 233 | 26 | 3-(2-Thienyl)propyl bromide and 1,6-dibromohexane | 9-(2-Thienyl)nonyl bromide |
| 234 | 17 | 6-(2-Furyl)hexanoic acid | 6-(2-Furyl)hexanol |
| 235 | 25 | 4-(2,5-Dimethyl-3-thienyl)-butyric acid | 4-(2,5-Dimethyl-3-thienyl)butanol |

TABLE VIII

The following aryl- or heteroarylalkynyl, alkenyl or alkylaminophenyl acetates are prepared from the appropriate alcohols or alkyl halides by the method shown. The requisite mesylates are prepared by the method of Example 9; ω-bromoalkylaminophenyl acetates are prepared by the method of Example 27.

| Example No. | Method of Example | 4-(Substituted-amino)phenylacetate esters |
|---|---|---|
| 236 | 28 | Ethyl 4-(14-phenyltetradec-13-ynylamino)phenylacetate |
| 237 | 28 | Ethyl 4-[8-(4-chlorophenyl)-7-methyloct-5-ynylamino]phenylacetate |
| 238 | 28 | Ethyl 4-[17-(4-chlorophenyl)heptadec-16-ynylamino]phenylacetate |
| 239 | 28 | Ethyl 4-[12-(4-methoxyphenyl)dodec-10-ynylamino]phenylacetate |
| 240 | 28 | Ethyl 4-[8-(2-furyl)oct-7-ynylamino]phenylacetate |
| 241 | 27 | Ethyl-4-[4-(2-pyridyl)but-3-ynylamino]phenylacetate |
| 242 | 27 | Ethyl 4-[10-(4-chlorophenyl)dec-9-enylamino]phenylacetate |
| 243 | 27 | Ethyl 4-(9-phenylnona-6,8-dienylamino)phenylacetate |
| 244 | 27 | Ethyl 4-(18-methyl-18-phenyloctadec-16-ynylamino)phenylacetate |
| 245 | 27 | Ethyl 4-[10-(2-thienyl)dec-9-enylamino]phenylacetate |
| 246 | 11 | Ethyl 4-[4-Fluorophenylprop-2-enylamino]phenylacetate |
| 247 | 11 | Ethyl 4-{3-[(5-octyl)-2-thienyl)]prop-2-enylamino}phenylacetate |
| 248 | 23 | Ethyl 4-{12-(4-chlorophenyl)heptadec-16-enylamino}phenylacetate |
| 249 | 23 | Ethyl 4-[8-(2-furyl)oct-7-ynylamino]phenylacetate |
| 250 | 11 | Ethyl 4-(1-methyl-3-phenylprop-2-enylamino)phenylacetate |
| 251 | 27 | Ethyl 4-[3-(4-chlorophenyl)propylamino]phenylacetate |
| 252 | 27 | Ethyl 4-{3-[(5-octyl)-2-thienyl]propylamino}phenylacetate |
| 253 | 28 | Ethyl 4-[8-(1-naphthyl)octylamino]phenylacetate |
| 254 | 28 | Ethyl 4-[(2-cycloheptyl-4-imidazolylmethyl)amino]phenylacetate |
| 255 | 28 | Ethyl 4-[(2-propyl-4-imidazolylmethyl)amino]phenylacetate |
| 256 | 13 | Ethyl 4-[(4-chlorophenyl)methylamino]phenylacetate |
| 257 | 13 | Ethyl 4-[(4-hydroxy-3-methoxyphenyl)methylamino]phenylacetate |
| 258 | 13 | Ethyl 4-[(5-octyl-2-thienylmethyl)amino]phenylacetate |
| 259 | 20 | Ethyl 4-[6-(1-imidazolyl)hexylamino]phenylacetate |
| 260 | 27 | Ethyl 4-[4-(2-thienyl)butylamino]phenylacetate |
| 261 | 27 | Ethyl 4-(11-phenylundecylamino)phenylacetate |

TABLE IX

The following aryl- or heteroarylalkynyl, alkenyl or alkylaminophenylacetic acids are prepared from the esters of Table VIII by the method of Example 7.

| Example No. | 4-(Substituted-amino)phenylacetic acids |
|---|---|
| 262 | 4-(14-Phenyltetradec-13-ynylamino)phenylacetic acid |
| 263 | 4-[8-(4-Chlorophenyl)-7-methyloct-5-ynylamino]phenylacetic acid |
| 264 | 4-[17-(4-Chlorophenyl)heptadec-16-ynylamino]phenylacetic acid |
| 265 | 4-[12-(4-Methoxyphenyl)dodec-10-ynylamino]phenylacetic acid |
| 266 | 4-[8-(2-Furyl)oct-7-ynylamino]phenylacetic acid |
| 267 | 4-[4-(2-Pyridyl)but-3-ynylamino]phenylacetic acid |
| 268 | 4-[10-(Chlorophenyl)dec-9-enylamino]phenylacetic acid |
| 269 | 4-(9-Phenylnona-6,8-dienylamino)phenylacetic acid |
| 270 | 4-(18-Methyl-18-phenyloctadec-16-ynylamino)phenylacetic acid |
| 271 | 4-[10-(2-Thienyl)dec-9-enylamino]phenylacetic acid |
| 272 | 4-[4-Fluorophenylprop-2-enylamino]phenylacetic acid |
| 273 | 4-{3-[(5-Octyl)-2-thienyl]prop-2-enylamino}phenylacetic acid |
| 274 | 4-[17-(4-Chlorophenyl)heptadec-16-enylamino)]phenylacetic acid |
| 275 | 4-[8-(2-Furyl)oct-7-ynylamino]phenylacetic acid |
| 276 | 4-(1-Methyl-3-phenylprop-2-enylamino)phenylacetic acid |
| 277 | 4-[3-(4-Chlorophenyl)propylamino]phenylacetic acid |
| 278 | 4-3-[(5-Octyl)-2-thienyl]propylamino phenylacetic acid |
| 279 | 4-[8-(1-Naphthyl)octylamino]phenylacetic acid |

TABLE IX-continued

The following aryl- or heteroarylalkynyl, alkenyl or alkylaminophenylacetic acids are prepared from the esters of Table VIII by the method of Example 7.

| Example No. | 4-(Substituted-amino)phenylacetic acids |
|---|---|
| 280 | 4-[(2-Cycloheptyl-4-imidazolyl)methylamino]phenylacetic acid |
| 281 | 4-[(2-Propyl-4-imidazolyl)methylamino]phenylacetic acid |
| 282 | 4-[(4-Chlorophenyl)methylamino]phenylacetic acid |
| 283 | 4-[(4-Hydroxy-3-methoxyphenyl)methylamino]phenylacetic acid |
| 284 | 4-[(5-Octyl-2-thienyl)methylamino]phenylacetic acid |
| 285 | 4-[6-(1-imidazolyl)hexylamino]phenylacetic acid |
| 286 | 4-[4-(2-Thienyl)butylamino]phenylacetic acid |
| 287 | 4-(11-Phenylundecylamino)phenylacetic acid |
| 288 | 4-[(11-(1-Imidazolyl)undecylamino]phenylacetic acid |
| 289 | 4-[6-(4-Chlorophenyl)hex-5-enylamino]phenylacetic acid |

TABLE X

The following aryl- or heteroarylalkynyl, alkenyl or alkylamino hydrocinnamates are prepared from the appropriate alcohols or alkyl halides by the method shown. Alcohols are converted to their corresponding mesylates by method of Example 9; ethyl ω-bromoalkylaminohydrocinnamates are prepared according to the method of Example 27.

| Example No. | Method of Example | 4-(Substituted-amino)hydrocinnamate esters |
|---|---|---|
| 290 | 28 | Ethyl 4-[7-(4-methoxyphenyl)hept-6-ynylamino]hydrocinnamate |
| 291 | 28 | Ethyl 4-[12-(4-fluorophenyl)dodec-11-ynylamino]hydrocinnamate |
| 292 | 28 | Ethyl 4-{10-[4-(2-propyl)phenyl]dec-9-ynylamino}hydrocinnamate |
| 293 | 28 | Ethyl 4-[6-(2-pyridyl)hex-5-ynylamino]hydrocinnamate |
| 294 | 27 | Ethyl 4-[5-(2-thienyl)pent-3-ynylamino]hydrocinnamate |
| 295 | 11 | Ethyl 4-(3-phenylprop-2-enylamino)hydrocinnamate |
| 296 | 27 | Ethyl 4-[10-(2-thienyl)dec-9-enylamino]hydrocinnamate |
| 297 | 27 | Ethyl 4-(15-phenylpentadec-13-enylamino)hydrocinnamate |
| 298 | 28 | Ethyl 4-[2-(3,7-dimethyl-2,6-octadienyl)-4-imidazolylmethylamino]hydrocinnamate |
| 299 | 11 | Ethyl 4-[3-(3-trifluoromethylphenyl)prop-2-enylamino]hydrocinnamate |
| 300 | 27 | Ethyl 4-{9-[2-(5-ethyl)thienyl]non-8-enylamino}hydrocinnamate |
| 301 | 23 | Ethyl 4-[6-(2-pyridyl)hex-5-enylamino]hydrocinnamate |
| 302 | 27 | Ethyl 4-[3-(4-chlorophenyl)propylamino]hydrocinnamate |
| 303 | 28 | Ethyl 4-[10-(4-methoxyphenyl)decylamino]hydrocinnamate |
| 304 | 28 | Ethyl 4-[12-(4-decyloxyphenyl)dodecylamino]hydrocinnamate |
| 305 | 28 | Ethyl 4-[4-(2-benzyl)imidazolylmethylamino]hydrocinnamate |
| 306 | 27 | Ethyl 4-[6-(2-furyl)hexylamino]hydrocinnamate |
| 307 | 27 | Ethyl 4-(4-phenylbutylamino)hydrocinnamate |
| 308 | 27 | Ethyl 4-(2-phenylbutylamino)hydrocinnamate |
| 309 | 13 | Ethyl 4-(4-chlorophenylmethylamino)hydrocinnamate |
| 310 | 20 | Ethyl 4-[12-(1-imidazolyl)dodecylamino]hydrocinnamate |
| 311 | 20 | Ethyl 4-[6-(1-imidazolyl)hexylamino]hydrocinnamate |

TABLE XI

The following aryl- or heteroarylalkynyl, alkenyl or alkylaminohydrocinnamic acids are prepared from the esters of Table X by the method of Example 7.

| Example No. | Hydrocinnamic Acids |
|---|---|
| 312 | 4-[7-(4-Methoxyphenyl)hept-6-ynylamino]hydrocinnamic acid |
| 313 | 4-[12-(4-Fluorophenyl)dodec-11-ynylamino]hydrocinnamic acid |
| 314 | 4-{10-[4-(2-Propyl)phenyl]dec-9-ynylamino}hydrocinnamic acid |
| 315 | 4-[6-(2-Pyridyl)hex-5-ynylamino]hydrocinnamic acid |
| 316 | 4-[5-(2-Thienyl)pent-3-ynylamino]hydrocinnamic acid |
| 317 | 4-[3-Phenylprop-2-enylamino]hydrocinnamic acid |
| 318 | 4-[10-(2-Thienyl)dec-9-enylamino]hydrocinnamic acid |
| 319 | 4-(16-Phenylpentadec-13-enylamino)hydrocinnamic acid |
| 320 | 4-[2-(3,7-Dimethyl-2,6-octadienyl)-4-imidazolylmethylamino]hydrocinnamic acid |
| 321 | 4-[7-(3-Bromophenyl)hept-6-enylamino]hydrocinnamic acid |
| 322 | 4-[3-(3-Trifluoromethylphenyl)prop-2-enylamino]hydrocinnamic acid |
| 323 | 4-{9-[2-(5-Ethyl)thienyl]non-8-enylamino}hydrocinnamic acid |
| 324 | 4-[6-(2-Pyridyl)hex-5-enylamino]hydrocinnamic acid |
| 325 | 4-[3-(4-Chlorphenyl)propylamino]hydrocinnamic acid |
| 326 | 4-[10-(4-Methoxyphenyl)decylamino]hydrocinnamic acid |
| 327 | 4-[12-(4-Decyloxyphenyl)dodecylamino]hydrocinnamic acid |
| 328 | 4-[4-(2-Benzyl-4-imidazolylmethyl)amino]hydrocinnamic acid |
| 329 | 4-[6-(2-Furyl)hexylamino]hydrocinnamic acid |
| 330 | 4-(4-Phenylbutylamino)hydrocinnamic acid |
| 331 | 4-(2-phenylbutylamino)hydrocinnamic acid |
| 332 | 4-(4-Chlorophenylmethylamino)hydrocinnamic acid |
| 333 | 4-[12-(1-Imidazolyl)dodecylamino]hydrocinnamic acid |
| 334 | 4-[6-(1-Imidazolyl)hexylamino]hydrocinnamic acid |
| 335 | 4-[2-(5-Octylthienyl)methylamino]hydrocinnamic acid |

TABLE XII

The following aryl- or heteroarylalkynyl, alkenyl or alkylaminocinnamates are prepared from the appropriate alcohols or alkyl halides by the method shown. Alcohols are converted to the required mesylates by method of Example 9.

| Example No. | Method of Example | Cinnamate Esters |
|---|---|---|
| 336 | 27 | Ethyl 4-[6-(4-methoxyphenyl)hex-3-ynylamino]cinnamate |
| 337 | 28 | Ethyl 4-[13-(2-thienyl)tridec-12-ynylamino]cinnamate |
| 338 | 28 | Ethyl 4-[4-(2-furyl)but-3-ynylamino]cinnamate |
| 339 | 27 | Ethyl 4-(5-methyl-5-phenylpent-3-enylamino)cinnamate |
| 340 | 27 | Ethyl 4-[11-(4-fluorophenyl)undec-10-enylamino]cinnamate |
| 341 | 27 | Ethyl 4-[12-(3-indolyl)dodec-11-enylamino]cinnamate |
| 342 | 11 | Ethyl 4-[3-(4-chlorophenyl)prop-2-enylamino]cinnamate |
| 343 | 11 | Ethyl 4-(1-methyl-3-phenylprop-2-enylamino)cinnamate |
| 344 | 28 | Ethyl 4-[14-(4-benzyloxyphenyl)tetradecylamino]cinnamate |
| 345 | 27 | Ethyl 4-[4-(2,5-dimethyl-3-thienyl)butamino]cinnamate |
| 346 | 27 | Ethyl 4-(10-phenyldecylamino)cinnamate |
| 347 | 13 | Ethyl 4-[2-(5-octylthienyl)methylamino]cinnamate |
| 348 | 28 | Ethyl 4-(4-heptyloxyphenylmethylamino)cinnamate |

TABLE XIII

The following aryl- or heteroarylalkynyl, alkenyl or alkylaminocinnamic acids are prepared from esters of Table XII by the method of Example 7.

| Example No. | Cinnamic Acids |
|---|---|
| 349 | 4-[6-(4-methoxyphenyl)hex-3-ynylamino]cinnamic acid |
| 250 | 4-[13-(2-thienyl)tridec-12-ynylamino]cinnamic acid |
| 351 | 4-[4-(2-furyl)but-3-ynylamino]cinnamic acid |
| 352 | 4-(5-methyl-5-phenylpent-3-enylamino)cinnamic acid |
| 353 | 4-[11-(4-fluorophenyl)undec-10-enylamino]cinnamic acid |
| 354 | 4-[12-(3-indolyl)dodec-11-enylamino]cinnamic acid |
| 355 | 4-[3-(4-chlorophenyl)prop-2-enylamino]cinnamic acid |
| 356 | 4-(1-methyl-3-phenylprop-2-enylamino)cinnamic acid |
| 357 | 4-[14-(4-benzyloxyphenyl)tetradecylamino]cinnamic acid |
| 358 | 4-[4-(2,5-dimethyl-3-thienyl)butylamino]cinnamic acid |
| 359 | 4-(10-phenyldecylamino)cinnamic acid |
| 360 | 4-[2-(5-octyl-2-thienyl)ethylamino]cinnamic acid |
| 361 | 4-(4-heptyloxyphenylmethylamino)cinnamic acid |
| 362 | 4-[13-(4-chlorophenyl)tridecylamino]cinnamic acid |

TABLE XIV

The following aryl- or heteroarylalkynyl, alkenyl, or alkylaminophenylpropiolates are prepared from the appropriate alcohols or alkyl halides by the method shown. The requisite mesylate are prepared by the method of Example 9.

| Example No. | Method of Example | 4-(Substituted-amino)phenylpropiolate esters |
|---|---|---|
| 363 | 28 | Ethyl 4-[13-(3,4-dichlorophenyl)tridec-12-ynylamino]phenyl propiolate |
| 364 | 27 | Ethyl 4-[4-(2-pyridyl)but-3-ynylamino]phenyl propiolate |
| 365 | 27 | Ethyl 4-(6-phenylhex-4-enylamino)phenyl propiolate |
| 366 | 27 | Ethyl 4-{15-[2-(5-methyl)furyl]pentadec-14-enylamino}phenyl propiolate |
| 367 | 11 | Ethyl 4-[3-(4-fluorphenyl)prop-2-enylamino]phenyl propiolate |
| 368 | 28 | Ethyl 4-[9-(2-thienyl)nonylamino]phenyl propiolate |
| 369 | 27 | Ethyl 4-(1-ethyl-2-phenylethylamino)phenyl propiolate |
| 370 | 28 | Ethyl 4-[2-(2-naphthyl)ethylamino]phenyl propiolate |
| 371 | 27 | Ethyl 4-[3-(4-chlorophenyl)propylamino]phenyl propiolate |

TABLE XV

The following aryl- or heteroarylalkynyl, alkenyl, or alkylaminophenylpropiolic acids are prepared from the esters of Table XIV by the method of Example 7.

| Example No. | Phenylpropiolic Acids |
|---|---|
| 372 | 4-[13-(3,4-dichlorophenyl)tridec-12-ynylamino]phenyl propiolic acid |
| 373 | 4-[4-(2-pyridyl)but-3-ynylamino]phenyl propiolic acid |
| 374 | 4-(6-phenylhex-4-enylamino)phenyl propiolic acid |
| 375 | 4-{15-[2-(5-methyl)furyl]pentadec-14-enylamino}phenyl propiolic acid |
| 376 | 4-[3-(4-fluorophenyl)prop-2-enylamino]phenyl propiolic acid |
| 377 | 4-[9-(2-thienyl)nonylamino]phenyl propiolic acid |
| 378 | 4-(1-ethyl-2-phenylethylamino)phenyl propiolic acid |
| 379 | 4-(2-(2-naphthyl)ethylamino]phenyl propiolic acid |
| 380 | 4-[3-(4-chlorophenyl)propylamino]phenyl propiolic acid |

TABLE XVI

The following aryl- or heteroarylalkynyl, alkenyl or alkylaminoacetophenones are prepared by the method of Example 29. The requisite mesylates are prepared by the method of Example 9.

| Ex. No. | 4-(Substituted-amino)acetophenones |
|---|---|
| 381 | 4-[9-(4-Chlorophenyl)non-8-ynylamino]acetophenone |
| 382 | 4-[16-(Pentafluorophenyl)hexadec-15-ynylamino]acetophenone |
| 383 | 4-(4-(2-Pyridyl)but-3-ynylamino]acetophenone |
| 384 | 4-[13-(2-Furyl)tridec-11-ynylamino]acetophenone |
| 385 | 4-(9-Phenylnona-6,8-dienylamino)acetophenone |
| 386 | 4-(18-Methyl-18-phenyloctadec-16-enylamino)acetophenone |
| 387 | 4-[3-(4-Chlorophenyl)prop-2-enylamino]acetophenone |
| 388 | 4-{3-[(5-Octyl)-2-thienyl]propylamino}acetophenone |
| 389 | 4-[13-(Chlorophenyl)tridecylamino]acetophenone |
| 390 | 4-[6-(2-Furyl)hexylamino]acetophenone |
| 391 | 4-[2-(4-Fluorophenyl)ethylamino]acetophenone |
| 392 | 4-(7-Phenylheptylamino)acetophenone |

TABLE XVII

The following aryl- or heteroarylalkynyl, alkenyl or alkylaminobenzonitriles are prepared from the appropriate halide or alcohol by the method of Example 30. The requisite mesylates are prepared by the method of Example 9.

| Example No. | 4-(Substituted-amino)benzonitriles |
|---|---|
| 393 | 4-[10-(5-Methyl-2-thienyl)dec-9-ynylamino]benzonitrile |
| 394 | 4-(7-Phenylhept-6-ynylamino)benzonitrile |
| 395 | 4-[18-(4-Chlorphenyl)octadec-17-ynylamino]benzonitrile |
| 396 | 4-[4-(3-Methylphenyl)but-3-ynylamino]benzonitrile |
| 397 | 4-(4-(2-Furyl)but-3-ynylamino]benzonitrile |
| 398 | 4-(9-Phenylnona-6,8-dienylamino)benzonitrile |
| 399 | 4-[11-(4-Fluorophenyl)undec-10-enylamino]benzonitrile |
| 400 | 4-[13-(2-Pyridyl)tridec-12-enylamino]benzonitrile |
| 401 | 4-[12-(3-Indolyl)dodec-11-enylamino]benzonitrile |
| 402 | 4-[10-(2-Thienyl)dec-9-enylamino]benzonitrile |
| 403 | 4-[12-(4-Decyloxyphenyl)dodecylamino]benzonitrile |
| 404 | 4-[8-(1-Naphthyl)octylamino]benzonitrile |
| 405 | 4-[9-(2-Thienyl)nonylamino]benzonitrile |
| 406 | 4-[4-(2,5-Dimethyl-3-thienyl)butylamino]benzonitrile |
| 407 | 4-(1-Ethyl-2-phenylethylamino)benzonitrile |
| 408 | 4-[14-(4-Benzyloxyphenyl)tetradecylamino]benzonitrile |

TABLE XVIII

The following aryl- or heteroarylalkynyl, alkenyl or alkylaminobenzaldehydes are prepared from the corresponding benzonitriles of Table XVII by the method of Example 31.

| Ex. No. | 4-(Substituted-amino)benzaldehydes |
|---|---|
| 409 | 4-[10-(5-Methyl-2-thienyl)dec-9-ynylamino]benzaldehyde |
| 410 | 4-(7-Phenylhept-6-ynylamino)benzaldehyde |
| 411 | 4-[18-(4-Chlorophenyl)octadec-17-ynylamino]benzaldehyde |
| 412 | 4-[4-(3-Methylphenyl)but-3-ynylamino]benzaldehyde |
| 413 | 4-(4-(2-Furyl)but-3-ynylamino]benzaldehyde |
| 414 | 4-(9-Phenylnona-6,8-dienylamino)benzaldehyde |
| 415 | 4-[11-(4-Fluorophenyl)undec-10-enylamino]benzaldehyde |
| 416 | 4-[13-(2-Pyridyl)tridec-12-enylamino]benzaldehyde |
| 417 | 4-[12-(3-Indolyl)dodec-11-enylamino]benzaldehyde |
| 418 | 4-[10-(2-Thienyl)dec-9-enylamino]benzaldehyde |
| 419 | 4-[12-(4-Decyloxyphenyl)dodecylamino]benzaldehyde |
| 420 | 4-[8-(1-Naphthyl)octylamino]benzaldehyde |
| 421 | 4-[9-(2-Thienyl)nonylamino]benzaldehyde |
| 422 | 4-[4-(2,5-Dimethyl-3-thienyl)butylamino]benzaldehyde |
| 423 | 4-(1-Ethyl-2-phenylethylamino)benzaldehyde |
| 424 | 4-[14-(4-Benzyloxyphenyl)tetradecylamino]benzaldehyde |

TABLE XIX

The following aryl- or heteroarylalkynyl, alkenyl or alkylaminophenyl butyrates are prepared from the appropriate mesylates by the method of Example 27. The requisite mesylates are prepared by the method of Example 9.

| Example No. | 4-(Substituted-amino)phenylbutyrate esters |
|---|---|
| 425 | Ethyl 4-[4-(2-phenylbutylamino)phenyl]butyrate |
| 426 | Ethyl 4-[4-(4-phenylbutylamino)phenyl]butyrate |
| 427 | Ethyl 4-[4-(15-phenylpentadec-13-enylamino)phenyl]butyrate |
| 428 | Ethyl 4-{4-[6-(2-furyl)hexylamino]phenyl}butyrate |
| 429 | Ethyl 4-{4-[10-(2-thienyl)dec-9-enylamino]phenyl}butyrate |
| 430 | Ethyl 4-{-[3-(4-chlorophenyl)propylamino]phenyl}butyrate |
| 431 | Ethyl 4-{4-[9-(5-ethyl-2-thienyl)non-8-enylamino]-phenyl}butyrate |
| 432 | Ethyl 4-{4-[5-(2-thienyl)pent-3-ynylamino]phenyl}butyrate |

TABLE XX

The following aryl- or heteroarylalkynyl, alkenyl or alkylaminophenylbutyric acids prepared from the esters of Table XIX by the method of Example 7.

| Example No. | 4-(Substituted-amino)phenylbutyric acids |
|---|---|
| 433 | 4-[4-(2-Phenylbutylamino)phenyl]butyric acid |
| 434 | 4-[4-(15-Phenylpentadec-13-enylamino)phenyl]butyric acid |
| 435 | 4-{4-[6-(2-Furyl)hexylamino]phenyl}butyric acid |
| 436 | 4-{4-[3-(4-Chlorophenyl)propylamino]phenyl}butyric acid |
| 437 | 4-{4-[5-(2-Thienyl)pent-3-ynylamino]phenyl}butyric acid |

TABLE XXI

The following esters are prepared by the methods shown from the carboxylic acids of Tables V, IX, XI, XIII, XV and XX or appropriate derivatives thereof obtained by the methods of Examples 32-36.

| Example No. | Method of Example | Ester |
|---|---|---|
| 438 | 37 | 2,3-Dihydroxypropyl 4-[11-(2-chloro-6-fluorophenyl)undec-10-ynylamino]benzoate |
| 439 | 37 | 2,3-Dihydroxypropyl 4-[(2-cycloheptyl)-4-imidazolylmethylamino]phenylacetate |
| 440 | 37 | 2,3-Dihydroxypropyl 4-[12-(4-fluorophenyl)dodec-11-ynylamino]hydrocinnamate |
| 441 | 37 | 2,3-Dihydroxypropyl 4-(5-methyl-5-phenyl-3-pentenylamino)cinnamate |
| 442 | 37 | 2,3-Dihydroxypropyl 4-[15-(5-methyl-2-furyl)pentadec-14-enylamino]propiolate |
| 443 | 37 | 2,3-Dihydroxypropyl 4-[4-(2-phenylbutylamino)phenyl]butyrate |
| 444 | 38 | Methyl 4-[(4-chlorophenyl)methylamino]phenylacetate |
| 446 | 38 | Isopropyl 4-[5-(2-thienyl)pent-3-ynylamino]hydrocinnamate |
| 447 | 38 | Methyl 4-[13-(2-thienyl)tridec-12-ynylamino]cinnamate |
| 448 | 38 | Isopropyl 4-[9-(2-furyl)nonylamino]propiolate |
| 449 | 38 | Methyl 4-[4-(15-phenylpentadec-13-enylamino)phenyl]butyric acid |
| 450 | 39 | 3-Hydroxypropyl 4-[16-(pentafluorophenyl)hexadec-15-ynylamino]benzoate |
| 451 | 39 | 2-Hydroxypropyl 4-[(5-octyl-2-thienyl)methylamino]phenylacetate |
| 452 | 39 | 4-Hydroxybutyl 4-[10-(2-thienyl)dec-9-enylamino]hydrocinnamate |
| 453 | 39 | 2-Hydroxypropyl 4-[3-(4-chlorophenyl)prop-2-enylamino]cinnamate |
| 454 | 39 | 3-Hydroxypropyl 4-(1-ethyl-2-phenylethylamino)propiolate |
| 455 | 39 | 2-Hydroxyethyl 4-{4-[6-(2-furyl)hexylamino]phenyl}butyrate |
| 456 | 40 | 2-Ethoxyethyl 4-[12-(3-methylphenyl)dodec-10-ynylamino]benzoate |
| 457 | 40 | 2-Methoxyethyl 4-[4-(2-thienyl)butylamino]phenylacetate |
| 458 | 40 | 2-Ethoxyethyl 4-[7-(3-bromophenyl)hept-6-enylamino]hydrocinnamate |
| 459 | 40 | 2-Methoxyethyl 4-[4-(4-benzyloxyphenyl)tetradecylamino]cinnamate |
| 460 | 40 | 2-Ethoxyethyl 4-[3-(4-chlorophenyl)propylamino]propiolate |
| 461 | 41 | Methyl 4-(11-phenylundecylamino)phenylacetate |
| 462 | 41 | Methyl 4-[6-(2-pyridyl)hex-5-enylamino]hydrocinnamate |
| 463 | 41 | Methyl 4-[13-(4-chlorophenyl)tridecylamino]cinnamate |
| 464 | 42 | 1-Methoxycarbonylpropyl 4-[8-(4-chlorophenyl)-7-methyloct-5-ynylamino]benzoate |
| 465 | 42 | 1-Ethoxycarbonylethyl 4-(13-phenyltridec-8-ynylamino)benzoate |
| 466 | 42 | 1-Ethoxycarbonylpropyl 4-[(2-propyl-4-imidazolyl)methylamino]phenylacetate |
| 467 | 42 | 1-Methoxycarbonylpropyl 4-[3-(4-chlorophenyl)propylamino]hydrocinnamate |
| 468 | 42 | 1-Ethoxycarbonylpropyl 4-[4-(2,5-dimethyl-3-thienyl)butylamino]cinnamate |
| 469 | 42 | 1-Ethoxycarbonylpropyl 4-[2-(2-naphthyl)ethylamino]propiolate |
| 470 | 42 | 1-Methoxycarbonylethyl 4-{4-[3-(4-chlorophenyl)propylamino]phenyl}butyrate |
| 471 | 43 | 1-Ethoxycarbonylethyl 4-(7-phenylhept-6-ynylamino)benzoate |
| 472 | 43 | 1-Ethoxycarbonylethyl 4-[18-(chlorophenyl)-17-methyloctadec-15-ynylamino]benzoate |
| 473 | 44 | 1-Carboxyethyl 4-[13-(2-furyl)tridec-11-ynylamino]benzoate |
| 474 | 44 | 1-Carboxypropyl 4-[5-(4-chlorophenyl)pent-3-ynylamino]benzoate |
| 475 | 44 | 1-Carboxyethyl 4-[6-(4-chlorophenyl)hex-5-enylamino]phenylacetate |
| 476 | 44 | 1-Carboxypropyl 4-[4-(2-benzyl-4-imidazolyl)methylamino]hydrocinnamate |
| 477 | 44 | 1-Carboxyethyl 4-(10-phenyldecylamino)cinnamate |
| 478 | 44 | 1-Carboxybutyl 4-(6-phenylhex-4-enylamino)propiolate |
| 479 | 44 | 1-Carboxyethyl 4-{4-[5-(2-thienyl)pent-3-ynylamino]phenyl}butyrate |
| 480 | 45 | 4-Chlorophenyl 4-[4-(2-pyridyl)but-3-ynylamino]benzoate |
| 481 | 45 | 4-Methylphenyl 4-[6-(1-imidazolyl)hexylamino]phenylacetate |
| 482 | 45 | 3-Pyridylmethyl 4-[10-(4-methoxyphenyl)dec-9-ynylamino]hydrocinnamate |
| 483 | 45 | 4-Pyridyl 4-[2-(5-octyl-2-thienyl)ethylamino]cinnamate |
| 484 | 45 | 2-Pyridyl 4-[3-(4-fluorophenyl)prop-2-enylamino]propiolate |
| 485 | 46 | O-[4-(9-Phenylnon-5-ynylamino)benzoyl]malic acid |
| 486 | 46 | O-{4-[4-(2-Furyl)but-3-ynylamino]benzoyl}malic acid |
| 487 | 46 | O-{4-[10-(5-Methyl-2-thienyl)dec-9-ynylamino]benzoyl}malic acid |
| 488 | 47 | 2-(Ethoxycarbonyl)vinyl 4-(4-phenylbut-3-ynylamino)benzoate |
| 489 | 47 | 2-(Ethoxycarbonyl)vinyl 4-[6-(4-chlorophenyl)hex-5-enylamino]phenylacetate |
| 490 | 47 | 2-(Ethoxycarbonyl)vinyl 4-[6-(2-furyl)hexylamino]hydrocinnamate |
| 491 | 47 | 2-(Ethoxycarbonyl)vinyl 4-(1-methyl-3-phenylprop-2-enylamino)cinnamate |
| 492 | 47 | 2-(Ethoxycarbonyl)vinyl 4-[13-(3,4-dichlorophenyl)tridec-12-ynylamino]propiolate |
| 493 | 47 | 2-(Ethoxycarbonyl)vinyl 4-[4-(2-phenylbutylamino)phenyl]butyrate |

TABLE XXII

The following amides are prepared from the carboxylic acids of Table V or appropriate derivatives thereof obtained by the methods of Examples 32-36.

| Example No. | Method of Example | Amide |
|---|---|---|
| 494 | 48 | 1-{4-[4-(4-Fluorophenyl)but-3-ynylamino]benzoyl}piperidine |
| 495 | 48 | 1-{4-[5-(2-Thienyl)pent-3-ynylamino]benzoyl}pyrrolidine |
| 496 | 49 | Ethyl 4-(7-phenylhept-3-ynylamino)hippurate |
| 497 | 49 | Ethyl 4-[4-(2-pyridyl)but-3-ynylamino]hippurate |
| 498 | 50 | N-{4-[13-(2-Furyl)tridec-11-ynylamino]benzoyl}glycine |
| 499 | 50 | N-{4-[7-(5-Ethyl-2-furyl)hept-6-ynylamino]benzoyl}glycine |
| 500 | 51 | 4-[17-(4-Chlorophenyl)heptadec-16-ynylamino]-N-(phenylsulfonyl)benzamide |
| 501 | 51 | 4-[13-(2-Furyl)tridec-11-ynylamino]-N-(phenylsulfonyl)benzamide |
| 502 | 52 | 4-[5-(4-Chlorophenyl)pent-3-ynylamino]-N-(methylsulfonyl)benzamide |
| 503 | 52 | 4-[4-(2-Pyridyl)but-3-ynylamino]-N-(methylsulfonyl)benzamide |
| 504 | 53 | N-{4-[8-(3-Methylphenyl)oct-7-ynylamino]benzoyl}alanine |
| 505 | 53 | N-{4-[5-(2-Thienyl)pent-3-ynylamino]benzoyl}alanine |
| 506 | 54 | N-{4-[9-(4-Chlorophenyl)non-8-ynylamino]benzoyl}benzamide |
| 507 | 54 | N-{4-[5-(2-Thienyl)pent-3-ynylamino]benzoyl}benzamide |

TABLE XXII-continued

The following amides are prepared from the carboxylic acids of Table V or appropriate derivatives thereof obtained by the methods of Examples 32–36.

| Example No. | Method of Example | Amide |
|---|---|---|
| 508 | 55 | N-{-[7-(4-Methoxyphenyl)hept-6-ynylamino]benzoyl}piperidine |
| 509 | 55 | N-{4-[8-(2-Furyl)oct-7-ynylamino]benzoyl}pyrrolidine |
| 510 | 56 | N-(2,3-Dihydroxypropyl)octadec-7-ynylamino]benzamide |
| 511 | 56 | N-(2,3-Dihydroxypropyl)-4-[9-(2-pyridyl)non-5-ynylamino]benzamide |

TABLE XXIII

The following acetophenones are prepared from the carboxylic acids of Table V or appropriate derivatives thereof obtained by the methods of Examples 32–36.

| Example No. | Method of Example | 4-(Substituted-amino)acetophenones |
|---|---|---|
| 512 | 57 | Diethyl 4-[5-(2-thienyl)pent-3-ynylamino]benzoylmalonate |
| 513 | 58 | tert-Butyl ethyl 4-[4-(2-pyridyl)but-3-ynylamino]benzoylmalonate |
| 514 | 59 | Ethyl 2-{4-[13-(2-furyl)tridec-11-ynylamino]benzoyl}acetoacetate |
| 515 | 60 | Ethyl 4-[17-(4-chlorophenyl)heptadec-16-ynylamino]benzoylacetate |
| 516 | 61 | 4-[8-(3-Methylphenyl)oct-7-ynylamino]benzoacetic acid |
| 517 | 62 | 4'-[7-(4-Methoxyphenyl)hept-6-ynylamino]-2-(methylsulfinyl)acetophenone |
| 518 | 63 | 4'-[5-(2-Thienyl)pent-3-ynylamino]-2-(phenylsulfinyl)acetophenone |
| 519 | 64 | 4'-[9-(4-Chlorophenyl)non-8-ynylamino]-2-(phenylsulfinyl)acetophenone |
| 520 | 65 | 3-{4-[8-(2-Furyl)oct-7-ynylamino]benzoyl}-2,4-pentanedione |
| 521 | 66 | Methyl 3-{4-[9-(2-pyridyl)non-5-ynylamino]benzoyl}propionate |
| 522 | 67 | 3-{4-[9-(2-Pyridyl)non-5-ynylamino]benzoyl}propionic acid |

I claim:

1. The method of inhibiting atherosclerotic lesion development in a mammal comprising the administration of an effective lesion-development inhibiting amount of a compound of the formula:

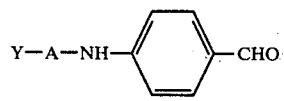

wherein A is a saturated or unsaturated alkylene group of 1–18 carbon atoms which may be branched or unbranched and Y is selected from the group consisting of phenyl, 1-naphthyl, 4-biphenylyl, 2-furyl, 2-thienyl, 3-thienyl, 4-thiazolyl, 2-imidazolyl, 4-imidazolyl, 2-pyridyl, 3-indolyl, 2-oxazolyl and each of the preceding moieties monosubstituted or disubstituted with alkyl, alkoxy or halogen with the proviso that the total number of carbon atoms in Y and A shall not exceed 24; and the pharmaceutically acceptable non-toxic acid-addition salts thereof to said mammal.

2. The method of claim 1 wherein said compound is administered to provide a daily dosage of from about one mg. to about 250 mg. per kilogram of body weight of said mammal.

3. An antiatherosclerotic composition in dosage-unit form useful for preventing or diminishing atherosclerotic lesion formation in mammals comprising from about one mg. to about 250 mg. per kilogram of body weight per daily dosage unit of a compound of claim 1.

4. A method of reducing regression of atherosclerotic lesion development in a mammal comprising administering to said mammal an effective lesion-regressive amount of a compound of claim 1.

5. A method of claim 4, wherein said compound is administered to provide a daily dosage of from about one mg. to about 250 mg. per kilogram of body weight of said mammal.

6. A method of treating hyperlipidemia and hyperlipoproteinemia in a mammal comprising administration to said mammal of an effective lipid-altering amount of a compound of claim 1.

7. A method of altering the lipoprotein pattern in a mammal comprising administration to said mammal of an effective lipid-altering amount of a compound of claim 1.

8. A compound selected from the group consisting of: 4-(p-chlorobenzylamino)benzladehyde; 4-[3-(p-chlorophenyl)propylamino]benzaldehyde; 4-[p-(tert-butyl)-benzylamino]benzaldehyde; 4-(p-fluorobenzylamino)benzaldehyde; 4-[3-(p-fluorophenyl)propylamino]benzaldehyde; 4-[10-(p-methoxyphenyl)decylamino]benzaldehyde; 4-[10-()5-methyl-2-thienyl)dec-9-ynylamino]benzaldehyde; 4-(7-phenylhept-6-ynylamino)benzaldehyde; 4-[18-(4-chlorophenyl)octadec-17-ynylamino]benzaldehyde; 4-[4-(3-methylphenyl)but-3-ynylamino]benzaldehyde; 4-[4-(2-furyl)-but-3-ynylamino]benzaldehyde; 4-(9-phenylnona-6,8-dienylamino)benzaldehyde; 4-[11-(4-fluorophenyl)undec-10-enylamino]benzaldehyde; 4-[13-(2-pyridyl)tridec-12-enylamino]benzaldehyde; 4-[12-(3-indolyl)dodec-11-enylamino]benzaldehyde; 4-[10-(2-thienyl)dec-9-enylamino]benzaldehyde; 4-[12-(4-decyloxyphenyl)dodecylamino]benzaldehyde; 4-[8-(1-naphthyl)octylamino]benzaldehyde; 4-[9-(2-thienyl)nonylamino]benzaldehyde; 4-[4-(2,5-dimethyl-3-thienyl)butylamino]benzaldehyde; 4-(1-ethyl-2-phenylethylamino)benzaldehyde; and 4-[14-(4-benzyloxyphenyl)tetradecylamino]benzaldehyde.

* * * * *